United States Patent [19]

White et al.

[11] Patent Number: 4,963,663

[45] Date of Patent: Oct. 16, 1990

[54] GENETIC IDENTIFICATION EMPLOYING DNA PROBES OF VARIABLE NUMBER TANDEM REPEAT LOCI

[75] Inventors: Raymond L. White; Yusuke Nakamura, both of Salt Lake City; Peter O'Connell, Midvale; Mark F. Leppert, Salt Lake City, all of Utah

[73] Assignee: University of Utah, Salt Lake City, Utah

[21] Appl. No.: 307,820

[22] Filed: Feb. 8, 1989

Related U.S. Application Data

[63] Continuation-in-part of Ser. No. 288,835, Dec. 23, 1988, abandoned, which is a continuation-in-part of Ser. No. 282,141, Dec. 8, 1988, abandoned, which is a continuation-in-part of Ser. No. 157,962, Feb. 18, 1988, abandoned.

[51] Int. Cl.$^5$ .................. C07H 21/04; C12Q 1/68; G01N 33/50
[52] U.S. Cl. .......................... 536/27; 435/6; 436/63; 935/10; 935/19; 935/29; 935/73; 935/78
[58] Field of Search ............... 435/6; 436/63; 536/27; 935/10, 19, 29, 73, 78

[56] References Cited

U.S. PATENT DOCUMENTS 4,861,708  8/1989  Frossard ............................. 435/6

OTHER PUBLICATIONS

Scambler et al. (1987) Nucleic Acids Res., vol. 15, No. 19, p. 8121.
Smeets et al. (1987) Nucleic Acids Res., vol. 15, No. 19, p. 8120.
Robbins et al., (1987) Nucleic Acids Res., vol. 15, No. 19, p. 8122.
Kato et al. (1983) Gene, vol. 26, pp. 53-57.
Huang, et al. (1987) J. of Biol. Chem. vol. 262 (19) pp. 8952-8955.
Botstein, D et al., *Am J Hum Genet* 32, 314 (1980).
Wyman & White, *Proc Natl Acad Sci* 77, 6754 (1980).
Bell, G et al., *Proc Natl Acad Sci* 78, 5759 (1981).
Weller, P et al., *Embo J* 3, 439 (1984).
White, R et al., *Nature* 313, 101 (1985).
Jeffreys, A et al., *Nature* 314, 67 (1985).
Jeffreys, A et al. *Nature* 316, 76 (1985).
Gill, P et al., *Nature* 318, 577 (1985).
Jeffreys, A et al. *Am J Hum Genet* 39, 11 (1986).
Kanter, et al., *J For Sci* 31, 403 (1986).
Giusti, A et al., *J For Sci* 31, 409 (1986).
Wong, Z et al., *Nucl Acids Res* 14, 4605 (1986).
Baird, M et al., *Am J Hum Genet* 39, 489 (1986).
Knowlton, R et al., *Blood* 68, 378 (1986).
Jeffreys, AJ, *Biochem Soc Trans* 15, 309 (1987).
Gill, P et al., *Electrophoresis* 8, 38 (1987).
Nakamura et al., *Science* 235, 1616 (1987).
Wong, Z et al., *Ann Hum Genet* 51, 269 (1987).
Nakamura, Y et al., *Nucl Acids Res* 15, 10073 (1987).
Nakamura, Y et al., *Nucl Acids Res* 15, 10607 (1987).
Nakamura, Y et al., *Nucl Acids Res* 15, 10609 (1987).
Nakamura, Y et al., *Nucl Acids Res* 16, 381 (1988).
Myers, R et al., *Nucl Acids Res* 16, 784 (1988).
Nakamura, Y et al., *Nucl Acids Res* 16, 786 (1988).
Nakamura, Y et al., *Nucl Acids Res* 16, 1229 (1988).
Fowler, S et al., *Hum Genet* 79, 142 (1988).
Jeffreys, A et al., *Nature* 332, 278 (1988).
Nakamura, Y et al., *Nucl Acids Res* 16, 3119 (1988).
Nakamura, Y et al., *Nucl Acids Res* 16, 3120 (1988).

(List continued on next page.)

*Primary Examiner*—Robert A. Wax
*Assistant Examiner*—Ardin H. Marschel
*Attorney, Agent, or Firm*—Venable, Baetjer, Howard & Civiletti

[57] ABSTRACT

The present invention is related to the identification of cloned DNA sequences that reveal individual multiallele loci. The loci are used in the process of the present invention to provide convenient and accurate genetic identification. A large number of clones that recognize VNTR loci have been isolated from a cosmid library and characterized.

38 Claims, 6 Drawing Sheets

GENETIC IDENTIFICATION EMPLOYING DNA PROBES OF VARIABLE NUMBER TANDEM REPEAT LOCI

CROSS REFERENCE TO RELATED APPLICATION

This application is a continuation-in-part of application Ser. No. 288,835, filed Dec. 23, 1988 which is a continuation-in-part of application Ser. No. 282,141, filed Dec. 9, 1988 which is a continuation-in-part of application Ser. No. 157,962 filed Feb. 18, 1988.

FIELD OF INVENTION

The present invention relates to methods and compositions for identifying human nucleic acid polymorphism. One application of the invention is determining the degree of similarity of individuals by comparing the nature of polymorphism of the individuals. Essentially, the nature of polymorphism in an individual serves as a tag or tracer of that individual. Particular applications include paternity testing, use in forensic medicine, disease diagnosis and determination of chimerism/mosaicism as in distinguishing zygosity or following transplantation.

BACKGROUND OF INVENTION

Population variation occurs by processes such as recombination and mutation. Variation can be found at the level of the organism, cell or cell component. Biological redundancy favors variation absent detriment to survival. For example, divergence of related nucleic acid sequences does not imply variability of the polypeptides those sequences encode.

The state of variability, particularly with reference to a protein or a nucleic acid, is known as polymorphism. Until recently, study of polymorphism focused on cell membrane proteins, serum-borne proteins or intracellular proteins. Applications include blood group typing, for example ABO or HLA, and isozyme analysis (Lewontin & Hubby, *Genetics* (1966) 54, 595). Those methods rely on amino acid changes that alter, for example, an antigenic determinant or molecular charge. But protein polymorphism may be 'silent' because the amino acid substitution does not cause a change that is recognizable by those methods. That could occur if the substitution occurs at a site that is normally unexposed in the tertiary or quarternary structure of the protein.

Those limitations have been circumvented with the observation of polymorphism in nucleic acids. The eukaryotic genome is comprised of three classes of sequences—unique, moderately repeated and highly repeated. Generally, the three classes are interspersed throughout the genome. Many of those sequences are of unknown function and may not encode requisite RNAs or proteins. Of those sequences known to encode proteins, most are composites of coding and noncoding segments. Nucleic acid variation can occur for example because of codon degeneracy or in areas where lack of selection pressures permits a high degree of polymorphism as in pseudogenes, highly repeated sequences or in noncoding regions of structural genes.

Nucleic acid polymorphism may be detectable as single base changes within restriction sites. Wyman and White (*Proc Natl Acad Sci USA* (1980) 77, 6754) found a locus in the human genome in which polymorphism resulted from DNA rearrangement. Subsequently, it was determined that the mechanism responsible for the polymorphism was varying number of a repeat sequence at that locus. Other sites where polymorphism is due to copy number differences were found near the α globin genes (Higgs et al., *Nucl Acids Res* (1981) 9, 4213), insulin gene (Bell et al., *Nature* (1982) 295, 31), zeta-globin genes (Proudfoot et al., *Cell* (1982) 31, 553; Goodbourn et al., (*Proc Natl Acad Sci USA* (1983) 80, 5022), c-Ha-ras-1 locus (Capon et al., *Nature* (1983) 302, 33) and myoglobin gene (Weller et al., *EMBO J* (1984) 3, 439).

Glassberg (GB2135774A) disclosed a method for genetic identification of individuals by analysis of DNA length polymorphism detected with clones developed by Wyman & White, supra, and Capon et al., supra. With regard to the Wyman & White clone, the repeat unit is 3bp which increases the likelihood of cross reactivity and the size of genomic fragments detected are 14kb or larger. Size differences of large fragments are sometimes difficult to resolve in agarose gel electrophoresis. The fragment sizes detected with the Capon clone are smaller but there are few alleles at that locus and each of a third of the alleles is present at less than 1% in a population of 268 random individuals. (The value of a locus for identification purposes is related directly to the number of alleles and the frequency of each allele in the population.)

Jeffreys (GB2166445A) found that many polymorphic regions have a sequence in common, which he called the core sequence. He constructed concatamers of core or quasi-core sequences which were then cloned. When used as probes of genomic DNA, those clones hybridized to a plurality of fragments. The difficulty associated with those clones is interpretation of the complex hybridization pattern.

The utility of clones that detect highly polymorphic loci is evidenced by papers describing their applicability in the study of cancer (Thein et al., *Br J Cancer* (1987) 55, 353); in forensic medicine (Gill et al., *Electrophoresis* (1987) 8, 38; Kanter et al., *J For Sci* (1986) 31, 403; Giusti et al., *J. For Sci* (1986)31, 409); in zygosity determination (Motomura et al., *Jpn J Hum Genet* (1987) 32, 9; Jones et al., *Eur J. Haematol* (1987) 39, 144; Hill et al., *Lancet* (1985) ii, 1394); detection of chimerism (Wallace et al., *Cold Spring Harb Symp Quant Biol* (1986) 51, 257; Knowlton et al., *Blood* (1986) 68, 378); in veterinary medicine (Morton et al., *Vet Rec* (1987) 121, 592; Jeffreys et al., *Anim Genet* (1987) 18, 1); in population studies (Wetton et al., *Nature* (1987) 327, 149); in linkage studies (Ponder et al., *Henry Ford Hosp Med J* (1987) 35, 161; Matthew et al., *J Med Genet* (1987) 24, 524); and for paternity testing (Jeffreys et al., *Nature* (1985) 316, 76; Jeffreys et al., *Nature* (1985) 316, 76).

Donis-Keller et al. (EP 0221633) disclosed methods and compositions useful for genotyping by analyzing RFLPs. The claimed clones carry unique sequence inserts and hybridize to unlinked loci. The clones fall into two categories. The first consists of clones that reveal base changes within a restriction site, and the second consists of clones that yield fragment length differences with at least three enzymes.

The above-described art suffer shortcomings. Generally, the clones hybridize to multiple fragments per sample. That complicates interpretation. Some clones arose from loci that are not highly multiallelic or many of the alleles are rare. That reduces their usefulness. Some of the clones hybridize with genomic fragments that tend to be large and difficult to resolve using standard filter hybridization. That demands genomic DNA with minimal degradation. Furthermore, assay conditions must be specific to minimize spurious cross-reactivity. Finally, each laboratory has a small set of clones to work with. Any one clone may be uninformative in a specific case. Moreover, in order to rule out variability due to de novo mutation, it is important to analyze more than one locus. It is preferable that the succeeding loci analyzed be unlinked to the first locus. Ideally, all loci analyzed are on different chromosomes. Thus, an improvement on the prior art would be a set of single locus clones consisting of a larger number of clones that detect multiallelic, heterozygous loci and are mapped.

A modification was disclosed by Jeffreys (GB2188323A) where he excised a band from a gel, cloned and used that insert as probe. That clone hybridizes to a single multiallelic locus and yields a blot that is easier to interpret. Jeffreys also screened a size-restricted library for recombinants carrying 'core' sequences. Inserts from 5 positive plaques hybridized under high stringency to unique loci and provided blots that were easily interpretable. Nevertheless, the genomic fragments recognized were often large leading to problems with resolution and DNA quality.

Nakamura et al. (*Science* (1987) 235, 1616) named a genetic sequence that contains tandem repeats at a single locus a variable number of tandem repeats (VNTR) locus. They used oligonucleotides to screen a cosmid library for recombinants carrying VNTR sequences. Positive clones were used as probe to determine whether they hybridize to VNTR loci in the human genome, and if so, to assess the degree of heterozygosity at those loci.

SUMMARY OF THE INVENTION

The instant invention relates to methods and compositions for detecting polymorphic loci in the human genome. The invention teaches how to obtain nucleic acid clones that carry sequences that arose from or include a VNTR locus. The clones are screened to detect gene sequences that are highly heterozygous. Moreover, the clones are selected to detect unique VNTR loci dispersed throughout the genome.

VNTR clones can distinguish individuals based on the alleles carried at one or more loci in their genome. Thus, VNTR clones can be used for paternity determination, in forensic applications, zygosity determination, determining degree of inbreeding, pedigree analysis, gene mapping or any other application that requires identification of an organism, organ, tissue, cell, subcellular component, part thereof or degradative product thereof.

A number of VNTR clones have been characterized and are described below. Advantages of the VNTR clone set are the number of informative clones, characterization of the clones with respect to map location and degree of heterozygosity and in general the genomic fragments detected are of lower molecular weight. Small-sized alleles facilitate resolution, enable identification without filter hybridization and ensure robustness in their application.

DETAILED DESCRIPTION OF THE INVENTION

Figure 1:
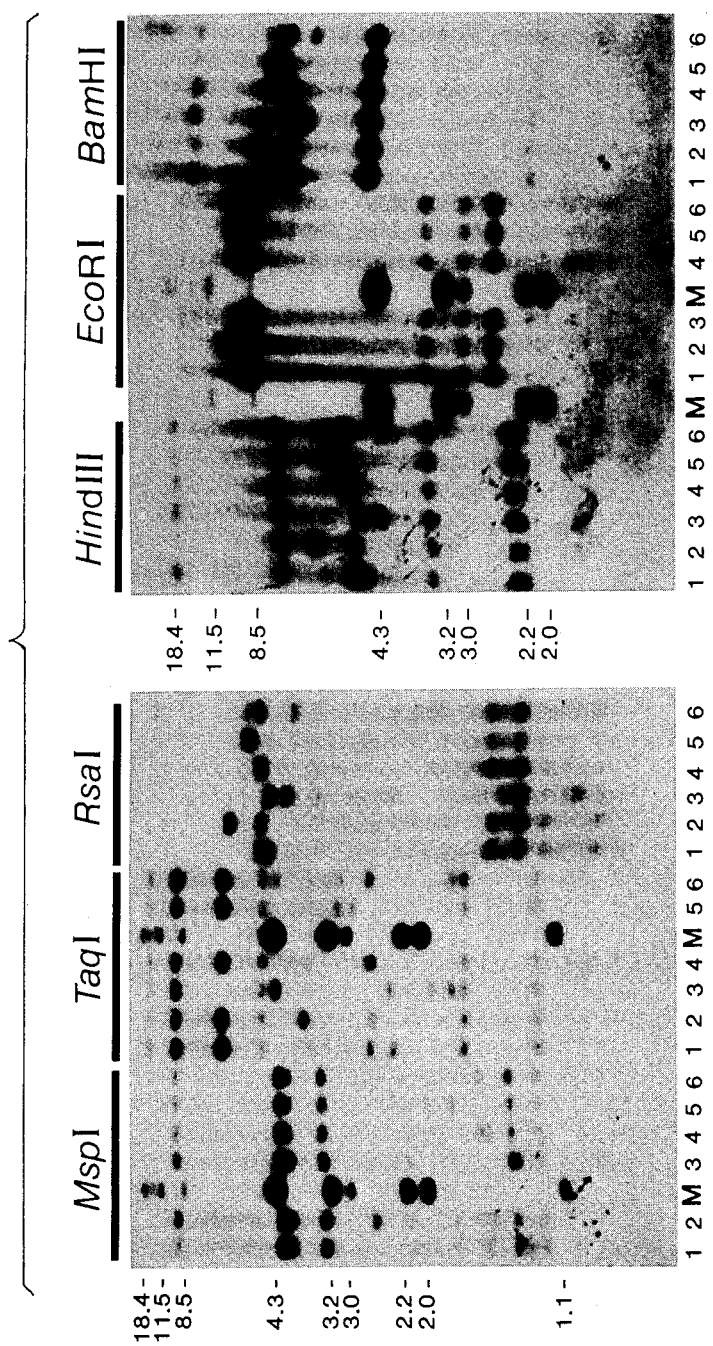
FIG. 1 comprises a pair of autoradiograms. The films depict random screening of six unrelated individuals. Cosmids were used as probe.

All of the terms used in the specification and the claims are known to one skilled in the act. Nevertheless, in order to provide a clear and consistent understanding of the specification and the claims, including the scope given to such terms, the following definitions are provided:

Clone: A vector-insert (foreign nucleic acid) recombinant nucleic acid molecule.

Clone set: An assemblage of recombinant nucleic acid molecules.

cM: Unit of map length. Related to % recombination, $\theta$ (the probability of recombination), the value—recombination fraction $\times$ 100, recombination frequency, crossover frequency.

Consensus: That which is held in common among an assemblage.

cXYZ: Is designation for a cosmid clone that hybridizes to the XYZ locus.

DpSq: Where D and S represent single copy DNA sequence, p is the number/letter of the chromosome to which the DNA maps (originated) and q is a counter. This symbol serves to identify a gene locus. Thus, if the X-linked gene locus known as XYZ is the first single copy DNA sequence mapped on the X chromosome, DXS1 is a synonym for XYZ.

Library or bank: A plurality of recombinant clones, said clones carry portions of foreign nucleic acid that originate in an organism, cell, chromosome or nucleic acid that in its entirely is too large to be cloned, said portions of foreign nucleic acid, when pieced together, are considered statistically to equal the starting material from which the pieces were obtained.

Mapping: Localizing a nucleic acid sequence within the genome to a chromosome, a region thereof, or within the nucleic acid that comprises a chromosome. Common techniques and tools of gene mapping include linkage analysis, test crosses, somatic cell hybrids, recombinant inbred strains and sequencing.

Nucleic Acid Fragment: A nucleotide polymer that can include an oligonucleotide but generally is longer than an oligonucleotide. As used herein, a nucleic acid fragment is intended to include a clone, the VNTR-containing fragment of a clone, a nucleic acid having substantial sequence homology to said VNTR-containing fragment and a nucleic acid which is capable of hybridizing to the single locus specified by the clone.

Oligo or oligonucleotide: A polymer of a few nucleotide bases.

Polymorphic locus or gene: A nucleic acid sequence localized in the diploid genome wherein the homologous copies are not identical.

pXYZ: Is designation for a plasmid clone that hybridizes to the XYZ locus.

Substantial sequence homology: Substantial functional and/or structural equivalence between sequences of nucleotides. Functional and/or structural differences between sequences having substantial sequence homology will be de minimis.

VNTR locus or region or sequence or gene: A nucleic acid tract that comprises multiple copies of a unit generally organized tandemly wherein said unit can be from 3 base pairs up through 40 base pairs or more in length, said tract may contain unique sequences interspersed between clusters of tandem repeats or flanking tandem repeats.

XYZ: Is a symbol that identifies a locus, also known as gene symbol. In this example, the name of the gene is XYZ.

The instant invention relates to methods and compositions for detecting polymorphic loci in humans. The nature of the loci carried by an individual is revealed by reacting VNTR clones with genomic DNA of that individual. That reaction is manifest commonly as a pattern of bands on a membrane support. Thus, a pattern is characteristic of an individual and patterns of individuals can be compared to determine if the individuals share a common origin.

The VNTR clones that fall within the scope of the instant invention detect unique loci dispersed throughout the human genome. The loci are polymorphic and the variability arises primarily by differences in copy number of tandem repeats. Those loci are called VNTR loci (Nakamura et al., supra). The instant invention teaches methods for identifying and producing in reagent quantities clones from VNTR loci. The value of a clone produced in the spirit of the invention increases directly with the number of alleles housed at that locus and the frequency of each allele. Ideally, one would hope for a multiallelic series with each allele present at the same frequency in a population. That goal is seldom met. In order to achieve a comparable degree of resolution, an alternative is to combine information from several, preferably unlinked loci. A discussion of gene mapping, recombinant DNA and population genetics may be found in Botstein et al. (*Am J Hum Genet* (1980), 32, 314).

Techniques which are utilized to obtain VNTR clones in accordance with the present invention are well known in the art. Suitable techniques are described in *Molecular Cloning* (1982) by Maniatis et al. and in Volumes 65, 68, 100, 101 and 152 of *Methods in Enzymology*. A more detailed description of procedures followed in the instant invention may be found also in Wyman and White, supra, Litt and White (*Proc Natl Acad Sci USA* (1985) 82, 6206) and Nakamura et al., supra.

As known in the art, hybridization with oligonucleotides requires well-defined sequences and assay conditions. Change of a single nucleotide or a degree at wash can alter the fidelity of recognition in a hybridization assay, as when using an oligo to probe a genomic digest for a unique sequence. On the other hand, when using an oligo to screen a library, particularly in the spirit of the instant invention, the goal is to obtain a reasonable number of positive clones. Thus, homology requirements are reduced, i.e. oligos may vary at one or more nucleotides or stringencies lowered to retain mismatched duplexes. VNTR clones may be obtained by screening a genomic library with oligonucleotides configured after known consensus sequences found at VNTR loci. Sequences of some of the oligos used are presented in Table 1.

TABLE 1

| | Oligonucleotides | | |
|---|---|---|---|
| | | Temperature (°C.) of: | |
| Oligonucleotide | Sequence | H* | W** |
| Zeta-globin (18 mer) | TGGGGCACAGGNTGTGAG | 42 | 48 |
| Insulin (14 mer) | ACAGGGGTGTGGGG | 30 | 37 |
| Myoglobin-1 (16 mer) | GGAGGTGGGCAGGAAG | 37 | 44 |
| Myoglobin-2 (14 mer) | GGAGGCTGGAGGAG | 37 | 42 |
| HBV-1 (16 mer) | GGAGTTGGGGGAGGAG | 37 | 44 |
| HBV-2 (20 mer) | GGACTGGGAGGAGTTGGGGG | 50 | 60 |
| HBV-3 (15 mer) | GGTGAAGCANAGGTG | 37 | 42 |
| HBV-4 (15 mer) | GAGAGGGGTGTAGAG | 37 | 42 |
| HBV-5 (15 mer) | GGTGTAGAGAGGGGT | 37 | 42 |
| YNZ22 (15 mer) | CTCTGGGTGTCGTGC | 37 | 42 |

*H is temperature of hybridization
**W is temperature of wash

Initially, a human genomic phage library was screened with the myoglobin-1 16mer. Low stringency conditions were chosen for hybridization to detect hybrids when homology between the oligonucleotide and genomic sequences was relatively low. About 50 positive clones per genome equivalent (250,000 clones) were obtained. However, when used to probe restriction digests of DNA from unrelated individuals, none revealed VNTR polymorphism. Because phage having repeated DNA sequences do not grow well in recA+ hosts, it appeared possible that the library constructed in recA+ bacteria had lost many phage that contained VNTR sequences.

Screening of a human cosmid library growing in recA− bacteria was more productive. Although the same conditions as for phage screening were used, three times as many positive clones per genome equivalent were obtained from the cosmid library as from the phage library (Table 2). As there are some similarities in sequence among the oligonucleotides set forth in Table 1, it is important to note that most of the cosmid clones identified with one oligonucleotide are different from those identified with another oligonucleotide. Fewer than 4% of cosmid clones hybridized with more than one of the oligonucleotides.

tions to that general rule are two VNTR loci with consensus sequences having an AT-rich motif. Those loci are linked to apolipoprotein B and collagen Type II as listed in Table 3.

TABLE 3

Comparison of the Consensus Sequences of VNTR Loci

| Locus/Linked Locus | Sequence |
| --- | --- |
| Zeta-globin | GGTTGTGAGTGGGGCACA |
| YNZ2 | GAGGCTCATGGGGCACA |
| YNZ132 | TGCAGGCTGTGGGTGTGATGGGTGA |
| Insulin | ACAGGGGTGTGGGG |
| YNI10 | CTGGGGGTGTGGGTGCTGCTCCAGGCTGTCAGATGCTCAC |
| THH59 | CTGGGGAGCCTGGGGACTTTCCACACC |
| YNH24 | CAGGAGCAGTGGGAAGTACAGTGGGGTTGTT |
| Consensus | GGGNNGTGGGG or GNNNGTGGG or GNNGTGGG |
| Harvey-ras (1) | GGGGGAGTGTGGCGTCCCCTGGAGAGAA |
| p3.4BHI (2) | AACAGTGCGTGGGCCACGTGAGCGGAGCAGGCTC |
| α-globin (3) | AACAGCGACACGGGGGG |
| D14S1 | NGG |
| Apolipoprotein B (4) | TTTTATAATTAATA |
| Collagen type II (5) | CAATATAGATAATATATACCTATATATTATTATA |

(1) Capon et al., supra.
(2) Silva, personal communication.
(3) Jarman et al., EMBO J (1986) 5, 1857.
(4) Knott et al., Nucl Acids Res (1986) 14, 9215.
(5) Stoker et al., ibid. (1985) 13, 4613

The sequencing data confirmed that variability arises in part from differences in the number of repeats. For example, partial sequences were obtained for three alleles at the D17S30 locus (YNZ22). The repeat unit is 70bp. The 6A allele contained four copies of the repeat, the 3A allele contained three copies of the repeat and the D7 allele contained two copies of the repeat. All repeat units of the three alleles had identical 70bp units.

But identity of repeat units need not be absolute. An allele of the D1S80 locus (MCT118) was sequenced and

TABLE 2

Summary of Screening for VNTR Polymorphism

| Screening Oligo | +Clones* | Clones Tested** | VNTR*** | Percent++ | Site Polymorphism+++ | |
| --- | --- | --- | --- | --- | --- | --- |
| Zeta-globin | 180 | 57 | 12 | 21 | 20 | (6) |
| Insulin | 220 | 20 | 4 | 20 | 8 | (1) |
| Myoglobin-1 | 150 | 65 | 8 | 12 | 19 | (8) |
| Myoglobin-2 | 18 | 18 | 8 | 44 | 8 | (2) |
| HBV-1 | 200 | 75 | 13 | 17 | 38 | (13) |
| HBV-2 | 40 | 15 | 2 | 13 | 10 | (3) |
| HBV-1 | 50 | 26 | 6 | 23 | 6 | (2) |
| HBV-2 and 3 | 150 | 58 | 15 | 26 | 40 | (19) |
| YNZ22 | 38 | 38 | 9 | 24 | 25 | (11) |
| Totals | 1046 | 372 | 77 | 21**** | 174 | (65) |

*Screened were one genomic equivalent (75,000 colonies) to two genomic equivalents for each probe. The number of positive clones per 75,000 colonies is shown.
**The number of clones that were hybridized to a panel of human genomic DNAs.
***The number of clones that hybridized to a VNTR locus.
****Mean value.
++The proportion of VNTR clones among the tested cosmids.
+++The number of cosmids that showed site polymorphisms with two or more restriction enzymes is shown in parentheses.

Several of the VNTR clones were sequenced using standard methodologies, generally the dideoxy technique of Sanger et al. (*Proc Natl Acad Sci USA* (1980) 74, 5463). A somewhat variable consensus sequence was identified. That sequence is GGGNNGTGGGG or in a broader sense an almost invariant sequence of GNNNGTGGG or GNNGTGGG applies. The excepten copies of a tandem repeat unit were found. The sequences of the ten units are as follows:
(1) CCCAAGG-AAGACAGA
(2) CCACAGGCAAGGAGGA
(3) CCACCGGAAAGGAAGA
(4) CCACCGGAAAGGAAGA (5) CCACCGGAAAGGAAGA
(6) CCACAGGCAAGGAGGA
(7) CCACCGGAAAGGAAGA
(8) CCACCGGCAAGGAGGA
(9) CCACCGGCAAGGAGGA
(10) CCACCAGGAAGGAGGA In that case, the repeat units are not reproduced exactly and another order of variability is imposed. The changes include deletion of a base in the first unit and transitions or transversions.

Because of the relatedness of VNTR clones, it is likely to obtain VNTR clones using oligonucleotides that are configured after the consensus sequence. Thus, an oligo of 14 or more bases containing a consensus or quasi-consensus sequence with the remaining bases chosen at random but preferably guanine or thymidine or cytosine can be used to screen a library for VNTR clones. The degree of sequence homology between an oligonucleotide and the consensus can be 50% or lower and it will remain possible to obtain VNTR clones from a library. In one experiment, an oligonucleotide of alternating T and G residues pulled out VNTR clones, one of which is pMCT118.

Because VNTR loci are dispersed throughout the genome, VNTR clones can be obtained randomly from a library by selecting and using clones as probe for a panel of genomic DNAs as described below. However, that can be a tedious and costly exercise with low return. An alternative is to use a library containing DNA from only a portion of the genome, as for example, a chromosome-specific library. In that case, a targeted portion of the genome is examined and the library contains fewer clones. Somatic cell hybrids (described below) or isolated chromosomes are a suitable source of human DNA for library construction. cTBQ7 was obtained in that fashion from a library containing somatic cell hybrid DNA wherein the only human chromosomes of the hybrid cell line are the 10 and Y. That cosmid clone was selected at random and used as probe of a panel of genomic DNAs from unrelated individuals to determine whether the clone hybridized to a polymorphic locus on either chromosome 10 or Y.

Candidate cosmid clones were used as probe for a panel of unrelated human genomic DNAs. Clones that hybridized under high stringency to a single polymorphic locus were subcloned, although that procedure was not entirely necessary. Subcloning entailed essentially fragmentation of the insert and finding the fragment or fragments that produced the same hybridization pattern as that of the originating cosmid clone. The trimmed fragments were subcloned generally into plasmids. In order to determine the degree of heterozygosity at the VNTR locus recognized by a clone, a larger number of DNAs from unrelated humans were analyzed. That analysis provided not only a measure of heterozygosity but data on the number of alleles, allele size (allele size is inferred from band size) and allele frequency. The DNAs were digested with several restriction enzymes to determine the enzyme producing the largest number of alleles and the smallest-sized alleles.

Sequence homology requirements change when using longer nucleic acid fragments as probe for unique sequences because the length and relative content of G/C pairs of the fragment contribute to hybridization kinetics and, thus, fidelity of pairing (see for example Wetmur and Davidson, *J Mol Biol* (1968) 31, 349). Hence, if one is performing an evolutionary survey of a gene sequence, hybridization conditions would be modified to accommodate sequence divergence due to genetic drift. (Nevertheless, the function of the sequences and the polypeptides encoded are conserved.) On the other hand, if the desire is to identify sequences at a particular locus, hybridization conditions are modified so that a high degree of complementarity of the hybridizing components is required to maintain the duplex. VNTR regions impose additional considerations in determining requisite sequence homology. Copy number variation contributes significantly to heterozygosity but often not all repeat units at a locus are identical. Thus, nucleic acid fragments that differ slightly in sequence may nevertheless hybridize to the same locus. Here, sequence homology may be defined in terms of those nucleic acid fragments that hybridize to a unique VNTR locus for indeed it is the VNTR locus and its detection that are paramount to the instant invention.

The VNTR clones can be fixed to the human genome map. There are several mapping techniques available, including linkage analysis and use of somatic cell hybrids. Many of the VNTR clones were mapped by linkage analysis, i.e. determining the inheritance of the marker in large pedigrees and comparing the pattern of presence/absence or size of the marker in question with those of loci previously studied in those same pedigrees. The power of linkage assessment increases with sample size and the number of loci studied within individual pedigrees. If patterns match perfectly, one can infer tight linkage of the marker with the anchoring gene(s) or identity of the marker with an anchoring gene. If the pattern match varies, one can infer partial linkage and map distances can be determined. It is preferred to use more than one anchoring gene. For a review of segregation, linkage analysis and the statistical bases of those treatments, see Cavalli-Sforza & Bodmer, *The Genetics of Human Populations* (1971).

Somatic cell hybrids are useful for rapid localization of a gene to a chromosome or chromosomal region. Weiss & Green, *Proc Natl Acad Sci USA* (1967) 58, 1104. Heterokaryons tend to segregate chromosomes randomly, except for the chromosomal region carrying the selectable marker. Thus, a panel of cell lines, each carrying one or more human chromosomes can be maintained. Panels are configured so that synteny with any one chromosome is determinable. The panel is screened for expression of or presence of a gene and association with particular chromosome(s) is ascertained. THH59 was mapped to chromosome 17 using somatic cell hybrids. Subsequently, linkage of THH59 and TK1 was found in family study. In addition, it is possible to obtain hybrid cell lines that carry human chromosomal fragments or translocations. If those rearrangements are identified, then linkage to a chromosomal region is possible. A similar technology for chromosomal localization is to use a panel of DNAs obtained from flow-sorted chromosomes. Deaven et al., *Cold Spring Harb Symp Quant Biol* (1986) 51, 159.

Family studies are particularly valuable for mapping and for clone identification. Cell lines established from members of extended multigeneration families serve as mapping and reference reagents with respect to alleles at a VNTR locus. Thus, the inheritance of specific alleles at a locus among selected members of a large kindred is a diagnostic tool for distinguishing a clone for that locus, derivatives of that clone, or clones with substantial sequence homology that hybridize to sequences at the locus. Such cell lines are available from the Human Genetic Mutant Cell Repository in Camden, New Jersey, or from the CEPH in Paris, France. For example, family 982, Utah Pedigree K-1331 represents a three-generation family and cell lines have been established from 15 members, including maternal and paternal grandparents, parents and nine children. To confirm that a subclone, new preparation of a clone or clone sent to another laboratory maintains specificity, it is used as probe for the cell line DNAs of Family 982 and the fragment pattern obtained is compared to the master pattern found when DNAs obtained from the family members themselves were analyzed with the original clone.

As of the date of the instant application, 45 clones suitable for the purposes detailed in the specification have been found. Information on the clones is summarized in Table 4 and detailed more specifically in Tables 5-35. In Tables 5-34, the name of the locus to which the clone hybridizes is denoted within parentheses in the title of the tables. For example, in Table 5, pYNH24 hybridizes to the D2S44 locus found on chromosome 2. In other words, the insert of pYNH24 originated from the genomic DNA at the D2S44 locus of human chromosome 2. Samples of *E. coli* harboring representative VNTR clones have been deposited with The American Type Culture Collection, 12301 Parklawn Drive, Rockville, Maryland, as indicated herein. Deposit is for the purpose of completeness but is not intended to limit the scope of the present invention to the materials deposited since the description as further illustrated by the Examples fully enables the practice of the instant invention. Access to the cultures will be available during the pendency of the patent application to those determined by the Commissioner of Patents and Trademarks to be entitled thereto. All restrictions on availability of said cultures to the public will be removed irrevocably upon the grant of the instant application and said cultures will remain available permanently during the term of said patent. Should any culture become nonviable or be destroyed, it will be replaced.

TABLE 4

VNTR Clones

| Clone | Enz | Alleles | ATCC Number | Deposit Date (d/m/y) |
|---|---|---|---|---|
| pYNH24 | HaeIII | 31 | 57570 | 1-4-87 |
| pCMM101 | HaeIII | >20 | 59372 | 14-4-88 |
| pYNZ22 | HinfI | >10 | 57574 | 1-4-87 |
| cEFD64 | HinfI | >10 | 57650 | 11-6-87 |
| pJCZ3.1 | HinfI | 7 | 57656 | 11-6-87 |
| cYNA13 | MspI | >10 | 59364 | 14-4-88 |
| pCMM86 | RsaI | >10 | 59682 | 13-12-88 |
| pEKMDA2I | AluI | 8 | 57554 | 1-4-87 |
| pJCZ16.2 | HinfI | >10 | 57658 | 11-6-87 |
| pJCZ67 | RsaI | >10 | 59362 | 14-4-88 |
| pMHZ47 | HaeIII | >10 | 59366 | 14-4-88 |
| pMLJ14 | HaeIII | >20 | 57578 | 1-4-87 |
| pCMM6 | TaqI | >10 | 59368 | 14-4-88 |
| pCMM66 | PstI | >10 | 59370 | 14-4-88 |
| pCMI327 | PvuII | >10 | 59680 | 13-12-88 |
| cEFD52 | PvuII | >10 | 59374 | 14-4-88 |
| pEFD139 | PstI | >10 | 59688 | 13-12-88 |
| pRMU3 | PvuII | >10 | 57564 | 1-4-87 |
| pMCT118 | HinfI | 17 | 59668 | 13-12-88 |
| pEFD126.3 | HinfI | 6 | 57624 | 11-6-87 |
| cCMM77 | PstI | >7 | 59690 | 13-12-88 |
| pMCOB17 | HinfI | 7 | 59686 | 13-12-88 |
| cYNA4 | MspI | >7 | 59672 | 13-12-88 |
| pMHZ10 | HinfI | 6 | 59674 | 13-12-88 |
| pMHZ13 | PstI | 8 | 59278 | 29-1-88 |
| cTBQ7 | TaqI | 8 | 59676 | 13-12-88 |
| cKKA39 | RsaI | 7 | 59678 | 13-12-88 |
| pYNZ21 | MspI | 8 | 59684 | 13-12-88 |

TABLE 4-continued

VNTR Clones

| Clone | Enz | Alleles | ATCC Number | Deposit Date (d/m/y) |
|---|---|---|---|---|
| pTHH33 | RsaI | >10 | 59670 | 13-12-88 |
| pTHH59 | PvuII | 6 | 57556 | 1-4-87 |
| cMLJ205 | MspI | >10 | 59692 | 13-12-88 |
| cMCT4 | | | 67881 | 2-2-89 |
| cMCT14 | | | 67881 | 2-2-89 |
| cMCT15 | | | 67881 | 2-2-89 |
| cMCT32 | | | 67881 | 2-2-89 |
| cMCT96 | | | 67881 | 2-2-89 |
| cMCT103 | | | 67881 | 2-2-89 |
| cMCT105 | | | 67881 | 2-2-89 |
| cMCT113 | | | 67881 | 2-2-89 |
| cMCT117 | | | 67881 | 2-2-89 |
| cMCT127 | | | 67881 | 2-2-89 |
| cMCT129 | | | 67881 | 2-2-89 |
| cMCT136 | | | 67881 | 2-2-89 |
| cMCT144 | | | 67881 | 2-2-89 |
| cMCT164 | | | 67881 | 2-2-89 |

TABLE 5

VNTR Clone pYNH24 on Chromosome 2 (D2S44)

Source/Description: A 2.0 kb MspI fragment from cYNH24 isolated by HBV-2 oligonucleotide was subcloned into the AccI site of pUC18.
Polymorphism: MspI identifies a >30 allele VNTR polymorphism with bands between 1.0-5.0 kb. TaqI, BglII, PvuII, PstI and BamHI also detect the polymorphism. Not polymorphic with RsaI.
Frequency: With MspI, 97% heterozygosity was observed in 120 unrelated Caucasians.
Chromosomal Localization: YNH24 has been assigned to chromosome 2 by multipoint linkage analysis with loci (APOB, D2S6) known to span that region.
Mendelian Inheritance: Codominant segregation of the MspI RFLP was observed in 44 three generation families.
Other Comments: RFLPs were observed under normal hybridization and wash stringencies. pYNH24 contains single sites for EcoRI and HindIII; an EcoRI/HindIII double digest yields two fragments of 2.7 and 2.1 kb; BglII digestion yields 3.6 kb and 1.1 kb fragments; and PvuII yields three fragments of 2.3, 1.7, and 0.8 kb.

| | Allele | Frequency |
|---|---|---|
| HaeIII 0.5-6.0 kb | 1 | 0.005 |
| | 2 | 0.005 |
| | 3 | 0.014 |
| | 4 | 0.005 |
| | 5 | 0.009 |
| | 6 | 0.045 |
| | 7 | 0.041 |
| | 8 | 0.059 |
| | 9 | 0.059 |
| | 10 | 0.068 |
| | 11 | 0.032 |
| | 12 | 0.014 |
| | 13 | 0.005 |
| | 14 | 0.059 |
| | 15 | 0.045 |
| | 16 | 0.027 |
| | 17 | 0.073 |
| | 18 | 0.050 |
| | 19 | 0.091 |
| | 20 | 0.045 |
| | 21 | 0.032 |
| | 22 | 0.055 |
| | 23 | 0.055 |
| | 24 | 0.023 |
| | 25 | 0.009 |
| | 26 | 0.014 |
| | 27 | 0.018 |
| | 28 | 0.018 |
| | 29 | 0.014 |
| | 30 | 0.009 |
| | 31 | 0.005 |

TABLE 6

VNTR Clone pCMM101 on Chromosome 14q (D14S13)

Source/Description: A 2.2 kb MspI fragment isolated by the myoglobin-2 oligonucleotide inserted into the AccI site of pUC18.
Polymorphism: HaeIII detects a >20 allele polymorphism.
Frequency: With HinfI, 84% heterozygosity was observed in 120 Caucasians.
Chromosomal Localization: Assigned to chromosome 14.
Mendelian Inheritance: Codominant segregation observed in 60 three generation families.

| | Allele | Frequency |
|---|---|---|
| HinfI 1.5–9.5 kb | 1 | 0.013 |
| | 2 | 0.031 |
| | 3 | 0.009 |
| | 4 | 0.027 |
| | 5 | 0.013 |
| | 6 | 0.013 |
| | 7 | 0.018 |
| | 8 | 0.027 |
| | 9 | 0.031 |
| | 10 | 0.0045 |
| | 11 | 0.031 |
| | 12 | 0.013 |
| | 13 | 0.022 |
| | 14 | 0.018 |
| | 15 | 0.022 |
| | 16 | 0.045 |
| | 17 | 0.040 |
| | 18 | 0.031 |
| | 19 | 0.0045 |
| | 20 | 0.058 |
| | 21 | 0.036 |
| | 22 | 0.067 |
| | 23 | 0.036 |
| | 24 | 0.063 |
| | 25 | 0.099 |
| | 26 | 0.076 |
| | 27 | 0.058 |
| | 28 | 0.076 |
| | 29 | 0.013 |
| | 30 | 0.009 |
| | 31 | 0.031 |

TABLE 7

VNTR Clone pYNZ22 on Chromosome 17p (D17S30)

Source/Description: A 2.7 kb BamHI fragment from cYNZ22 isolated by zeta-globin oligonucleotide was subcloned into the BamHI site of pBR322.
Polymorphism: MspI identifies a more than ten allele VNTR polymorphism with bands between 0.5 kb and 1.3 kb. TaqI, RsaI, BamHI, PstI and HindIII also detect the polymorphism. BglII and EcoRI do not optimally resolve the polymorphism.
Frequency: 86% heterozygosity was observed in 120 unrelated Caucasians with HinfI.
Chromosomal Localization: The locus was assigned to chromosome 17p by multipoint linkage analysis with loci (D17S1, MYH2, D17Z1) known to span that region.
Mendelian Inheritance: Codominant segregation has been observed in 30 three generation families.
Other Comments: RFLPs were observed under normal conditions of hybridization and washing. pYNZ22 contains unique sites for HindIII, EcoRI and SalI. PstI liberates 4.3 kb and 2.7 kb fragments. An independent screen of a cosmid library identified cJCZ16.2 which was subsequently shown to have substantial sequence homology with pYNZ22.

| | Allele | Frequency |
|---|---|---|
| HinfI 0.5–2.0 kb | 1 | 0.005 |
| | 2 | 0.009 |
| | 3 | 0.045 |
| | 4 | 0.050 |
| | 5 | 0.041 |
| | 6 | 0.050 |
| | 7 | 0.072 |
| | 8 | 0.032 |
| | 9 | 0.018 |
| | 10 | 0.018 |
| | 11 | 0.014 |

TABLE 7-continued

VNTR Clone pYNZ22 on Chromosome 17p (D17S30)

| | 12 | 0.099 |
|---|---|---|
| | 13 | 0.252 |
| | 14 | 0.162 |
| | 15 | 0.094 |
| | 16 | 0.036 |
| | 17 | 0.005 |

TABLE 8

VNTR Clone cEFD64 on Chromosome 3 (D3S42 and D3S46)

Source/Description: cEFD64 was isolated by the HBV-3 oligonucleotide.
Polymorphism: AluI identifies a 9 allele VNTR polymorphism with bands between 0.5 and 2.5 kb. RsaI, HaeIII, PstI, TaqI, EcoRI, BamHI, HindIII and PvuII also identify the polymorphism. Not polymorphic for BglII.
Frequency: With RsaI, 85% heterozygosity was observed in 80 unrelated Caucasians.
Chromosomal Localization: EFDA64 has been assigned to chromosome 3 by linkage analysis with APOD previously mapped to that chromosome.
Mendelian Inheritance: Codominant segregation of the RsaI RFLP was observed in 40 three generation families.
Other Comments: RFLPs were observed under normal hybridization and washing condition. Two TaqI insert fragments of cEFD64 have been subcloned in pUC18. They are designated as pEFD64.1 (D3S42, ATCC #59354, 14/4/88) and pEFD64.2 (D3S46, ATCC #57650, 11/6/87). Both hybridize to the VNTR locus.

| | Allele | Frequency |
|---|---|---|
| HinfI 1.0–5.5 kb | 1 | 0.004 |
| | 2 | 0.160 |
| | 3 | 0.022 |
| | 4 | 0.004 |
| | 5 | 0.211 |
| | 6 | 0.039 |
| | 7 | 0.009 |
| | 8 | 0.009 |
| | 9 | 0.004 |
| | 10 | 0.405 |
| | 11 | 0.017 |
| | 12 | 0.004 |
| | 13 | 0.004 |
| | 14 | 0.004 |
| | 15 | 0.004 |
| | 16 | 0.004 |
| | 17 | 0.095 |

TABLE 9

VNTR Clone pJCZ3.1 on Chromosome 19 (D19S20)

Source/Description: A 4.5 kb PstI fragment from cJCZ3 isolated by zeta-globin oligonucleotide was subcloned into the PstI site of pUC18.
Polymorphism: HinfI identifies a >10 allele VNTR polymorphism with bands between 1.4–4.0 kb. MspI, TaqI, RsaI, BglII, BamHI, PstI and PvuII also identify the polymorphism.
Frequency: With HinfI, 84% heterozygosity was observed in 120 unrelated Caucasians.
Chromosomal Localization: JCZ3.1 has been assigned to chromosome 19 by multipoint linkage analysis with loci (LDLR, APOC2) known to span that region.
Mendelian Inheritance: Codominant segregation of the HinfI RFLP was observed in 54 three generation families.
Other Comments: RFLPs were observed under normal hybridization and wash stringencies.

| | Allele | Frequency |
|---|---|---|
| HinfI 1.5–4.5 kb | 1 | 0.005 |
| | 2 | 0.040 |
| | 3 | 0.009 |
| | 4 | 0.005 |
| | 5 | 0.022 |
| | 6 | 0.005 |
| | 7 | 0.035 |
| | 8 | 0.005 |

TABLE 9-continued

VNTR Clone pJCZ3.1 on Chromosome 19 (D19S20)

| | |
|---|---|
| 9 | 0.292 |
| 10 | 0.013 |
| 11 | 0.093 |
| 12 | 0.053 |
| 13 | 0.031 |
| 14 | 0.050 |
| 15 | 0.084 |
| 16 | 0.261 |

TABLE 10

VNTR Clone cYNA13 on Chromosome 1 (D1S74)

Source/Description: cYNA13 was isolated with YNH24-related oligonucleotide (GGAGCAGTGGGNNNTACA) from a human genomic cosmid library.
Polymorphism: MspI identifies a more than 20 allele polymorphism with bands between 2.0 kb and 7.0 kb. RsaI, TaqI, BglII, PstI and PvuII also detect the polymorphism.
Frequency: 97% heterozygosity was observed in 106 unrelated Caucasians.
Chromosomal Location: The locus has been assigned to distal chromosome 1q by multipoint linkage analysis with loci (NRAS, PGM1, RH) known to span that region.
Mendelian Inheritance: Codominant segregation demonstrated in 53 three generation families.
Other Comments: RFLPs were observed after competitive hybridization with total human DNA. Digestion of cYNA13 with BamHI yields 3 fragments of 18.0, 5.0 and 4.1 kb.

| | Allele | Frequency |
|---|---|---|
| AluI 1.5–13.0 kb | 1 | 0.029 |
| | 2 | 0.100 |
| | 3 | 0.150 |
| | 4 | 0.163 |
| | 5 | 0.158 |
| | 6 | 0.110 |
| | 7 | 0.067 |
| | 8 | 0.048 |
| | 9 | 0.052 |
| | 10 | 0.029 |
| | 11 | 0.024 |
| | 12 | 0.005 |
| | 13 | 0.019 |
| | 14 | 0.014 |
| | 15 | 0.005 |
| | 16 | 0.005 |
| | 17 | 0.014 |
| | 18 | 0.009 |

TABLE 11

VNTR Clone pCMM86 on Chromosome 17q (D17S74)

Source/Description: A 4.3 kb MspI fragment from cCMM86 isolated by myoglobin-2 oligonucleotide was subcloned into the AccI site of pUC18.
Polymorphism: HinfI identifies a more than ten allele VNTR polymorphism with bands between 1.0 kb and 3.5 kb. HaeIII, TaqI, MspI, RsaI, and BglII also detect the polymorphism. Not polymorphic for PstI.
Frequency: 91% heterozygosity was observed in 604 individuals.
Chromosomal Localization: The locus was assigned to chromosome 17 by multipoint linkage analysis with loci (D17S1, MYH2, D17Z1) known to span that region.
Mendelian Inheritance: Codominant segregation has been observed in 50 three generation families.
Other Comments: RFLPs were observed under normal conditions of hybridization and washing. A subclone of cosmid CMM73 was shown to have substantial sequence homology with pCMM86. An example of redundancy in libraries.

TABLE 12

VNTR Clone pEKMDA2I on Chromosome 16 (D16S83)

Source/Description: A 3.5 kb RsaI fragment of cEKMDA2 was subcloned into the HincII site of pUC18.
Polymorphism: HinfI identified a >10 allele polymorphism with bands between 0.8–1.5 kb. TaqI, RsaI, BglII, PstI, EcoRI, BamHI, HindIII and PvuII also identify the polymorphism.
Frequency: 89% heterozygosity was observed in 102 unrelated Caucasians.
Chromosomal Localization: Assigned to chromosome 16 by linkage with HBZP1.
Mendelian Inheritance: Codominant segregation was observed in 50 three generation families.
Other Comments: RFLPs observed under normal assay conditions. pEKMDA2I does not contain an AccI site; contains unique sites for EcoRI and HindIII; BamHI digestion yields 3.4 kb and 2.9 kb fragments; and PstI yields 3.4 kb and 1.0 kb fragments.

| | Allele | Frequency |
|---|---|---|
| AluI 0.5–25 kb | 1 | .005 |
| | 2 | .009 |
| | 3 | .023 |
| | 4 | .023 |
| | 5 | .023 |
| | 6 | .069 |
| | 7 | .055 |
| | 8 | .097 |
| | 9 | .106 |
| | 10 | .161 |
| | 11 | .014 |
| | 12 | .194 |
| | 13 | .005 |
| | 14 | .134 |
| | 15 | .065 |
| | 16 | .018 |

TABLE 13

VNTR Clone pJCZ67 on Chromosome 7 (D7S396)

Source/Description: A 3.4 kb MspI fragment from cJCZ67 identified by the zeta-globin oligonucleotide cloned into the AccI site of pUC18.
Polymorphism: RsaI identifies greater than 10 alleles with bands between 3.0 and 6.0 kb. MspI, PstI, EcoRI, BamHI, BglII, PvuII and TaqI also detect the polymorphism.
Frequency: With MspI, 83% heterozygosity was observed in 57 unrelated Caucasians.
Chromosomal Localization: JCZ67 has been assigned to chromosome 7 by multipoint linkage analysis with loci (COL1A2, TCRG) known to span that region. It is ~30 cm distal to YNB3.1R on 7q.
Mendelian Inheritance: Codominant segregation for the RsaI polymorphism has been observed in 29 three generation families.
Other Comments: RFLPs were observed under normal hybridization and wash stringencies.

TABLE 14

VNTR Clone cMHZ47 on Chromosome 13 (D13S52)

Source/Description: The cosmid was isolated by the YNZ22 oligonucleotide.
Polymorphism: MspI identifies a >10 allele VNTR polymorphism with bands between 1.5–3.0 kb. TaqI, HaeIII, RsaI, PvuII, EcoRI, BamHI and HindIII also detect the polymorphism.
Frequency: With MspI, 83% heterozygosity was observed in 99 unrelated Caucasians.
Chromosomal Localization: MHZ47 has been assigned to distal chromosome 13q by multipoint linkage analysis with loci (D13S6, D13S1, ESD, D13S4) known to span that region. It is ~30 cM distal to p9A7 on 13q.
Mendelian Inheritance: Codominant segregation was observed in 50 three generation families.
Other Comments: RFLPs were observed under hybridization with total human DNA. Digestion of cMHZ47 with the

TABLE 14-continued

VNTR Clone cMHZ47 on Chromosome 13 (D13S52)

following enzymes yields multiple fragments: HindIII-5.9 kb (doublet), 4.4 kb, 3.5 kb, 0.9 kb; EcoRI-8.2 kb, 6.6 kb, 4.6 kb, 3.1 kb; and TaqI-3.8 kb, 2.0 kb, 1.8 kb, 1.5 kb, 1.2 kb.

TABLE 15

VNTR Clone pMLJ14 on Chromosome 14q (D14S13)

Source/Description: A 2.4 kb MspI fragment from cMLJ14 isolated using the myoglobin-1 oligo was subcloned into the AccI site of pUC18.
Polymorphism: RsaI identifies a >20 allele polymorphism with bands between 2-13 kb. MspI, AluI, HaeIII, BglII, TaqI, BamHI, EcoRI, HindIII, PvuII and PstI also detect the polymorphism.
Frequency: With RsaI, 95% heterozygosity was observed among 120 unrelated Caucasians.
Chromosomal Localization: MLJ14 has been assigned to chromosome 14 by multipoint linkage analysis with loci (PI, D14S1, MHZ9, GM, IGHC) known to span that region.
Mendelian Inheritance: Codominant segregation of the polymorphism was observed in 54 three generation families.
Other Comments: RFLPs were observed under hybridization with total human DNA. Digestion of pMLJ14 with EcoRI and HindIII yields a 2.7 kb and a 2.4 kb fragment consistent with unique sites for each enzyme.

| AluI 1.0-6.5 kb | Allele | Frequency |
|---|---|---|
| | 1 | 0.031 |
| | 2 | 0.005 |
| | 3 | 0.020 |
| | 4 | 0.046 |
| | 5 | 0.010 |
| | 6 | 0.026 |
| | 7 | 0.031 |
| | 8 | 0.010 |
| | 9 | 0.020 |
| | 10 | 0.010 |
| | 11 | 0.041 |
| | 12 | 0.010 |
| | 13 | 0.010 |
| | 14 | 0.020 |
| | 15 | 0.020 |
| | 16 | 0.010 |
| | 17 | 0.010 |
| | 18 | 0.015 |
| | 19 | 0.041 |
| | 20 | 0.046 |
| | 21 | 0.061 |
| | 22 | 0.041 |
| | 23 | 0.082 |
| | 24 | 0.066 |
| | 25 | 0.077 |
| | 26 | 0.005 |
| | 27 | 0.143 |
| | 28 | 0.036 |
| | 29 | 0.005 |
| | 30 | 0.036 |
| | 31 | 0.015 |
| | 32 | 0.010 |

TABLE 16

VNTR Clone pCMM6 on Chromosome 20 (D20S19)

Source/Description: A 4.0 kb PstI fragment from cCMM6 isolated by myoglobin-1 oligonucleotide was subcloned into the PstI site of pUC18.
Polymorphism: TaqI identifies a more than 10 allele VNTR polymorphism with a band between 2.3 and 6.0 kb. MspI, RsaI, PvuII and PstI also show the same polymorphism. Not polymorphic for BglII.
Frequency: With TaqI, 90% heterozygosity was observed in 78 unrelated Caucasians.
Chromosomal Localization: The locus was assigned to chromosome 20 by linkage analysis with a locus (D20S1)

TABLE 16-continued

VNTR Clone pCMM6 on Chromosome 20 (D20S19)

known to be on that chromosome.
Mendelian Inheritance: Codominant segregation has been observed in 44 three generation families.
Other Comments: RFLPs were observed under normal conditions of hybridization and washing.

TABLE 17

VNTR Clone pCMM66 on Chromosome 14 (D14S22)

Source/Description: A 4.8 kb TaqI fragment from cCMM66 isolated by the myoglobin-2 oligonucleotide was subcloned into the AccI site of pUC18.
Polymorphism: PstI identifies a >10 allele VNTR polymorphism with a variable band between 4.0 and 6.0 kb. RsaI also shows the polymorphism. Not polymorphic for MspI or TaqI.
Frequency: The heterozygosity of the locus in 67 unrelated Caucasians is 85% with PstI.
Chromosomal Localization: CMM66 has been assigned to chromosome 14q by multipoint linkage analysis with loci (D14S1, GM, PI) known to span that region.
Mendelian Inheritance: Codominant segregation of the PstI RFLP was observed in 34 three generation families.
Other Comments: RFLPs were observed under hybridization with total human DNA.

TABLE 18

VNTR Clone pCMI327 (D17)

Source/Description: Isolated by the insulin oligonucleotide and subcloned in pUC18.
Polymorphism: PvuII reveals a greater than 10 allele polymorphism with bands between 2.5 and 4 kb.
Frequency: The locus shows a heterozygosity of 83%.
Chromosomal Localization: CMI327 has been mapped to chromosome 17 by linkage analysis. CMI327 showed linkage to HtK9, THH59 and AC256.
Other Comments: RFLPs observed under normal conditions.

TABLE 19

VNTR Clone cEFD52 on Chromosome 17q (D17S26)

Source/Description: The cosmid was isolated by the HBV-4 oligonucleotide.
Polymorphism: PvuII best resolves a >10 allele VNTR polymorphism with bands between 5.0-10.0 kb. MspI, HaeIII, AluI, TaqI, RsaI, BglII and PstI also detect the polymorphism.
Frequency: With PvuII, 90% heterozygosity was observed in 96 unrelated Caucasians.
Chromosomal Localization: EFD52 has been assigned to chromosome 17q by multipoint linkage analysis with loci (D17Z1, TK1, THH59) known to span that region.
Mendelian Inheritance: Codominant segregation demonstrated in 48 families.
Other Comments: cEFD52 was pre-associated with excess human DNA prior to hybridization. Otherwise, RFLPs were observed under normal conditions of hybridization and washing.

TABLE 20

VNTR Clone pEFD139 (D22)

Source/Description: A 15 kb PvuII fragment obtained by the HBV-3 oligonucleotide subcloned into the HincII site of pUC18.
Polymorphism: PvuII reveals an 8 allele polymorphism as do BglII and PstI. With PstI, the bands range from 5-8 kb.
Frequency: The locus heterozygosity is 85%.

TABLE 20-continued
VNTR Clone pEFD139 (D22)

Chromosomal location: EFD139 has been mapped by linkage analysis to HSA22.
Other Comments: RFLPs observed under normal conditions.

TABLE 21
VNTR Clone pRMU3 on Chromosome 17q (D17S24)

Source/Description: A BamHI-SacI fragment from cRMU1 was subcloned into the larger fragment following BamHI-SacI double digestion of pUC18.
Polymorphism: PvuII identifies a >10 allele polymorphism with bands between 0.7 kb and 1.3 kb. TaqI works almost as well yielding >6 alleles between 2.2 and 2.7 kb. MspI, RsaI, BamHI also detect the polymorphism. PstI and HindIII do not adequately resolve the polymorphism.
Frequency: With TaqI, 85% heterozygosity was observed in 96 unrelated Caucasians.
Chromosomal Localization: The locus has been assigned to distal chromosome 17q by multipoint linkage analysis with loci (D17Z1, TK1, THH59) known to span that region.
Mendelian Inheritance: Codominant segregation observed in 48 three generation families.
Other Comments: RFLPs were observed under normal hybridization stringency.

TABLE 22
VNTR Clone pMCT118 on Chromosome 1p (D1S80)

Source/Description: A 3.1 kb PstI fragment from cMCT118 isolated with an oligonucleotide (GTGTGTGTGTGTGTGTGTGT) was subcloned into the PstI site of pUC18.
Polymorphism: HinfI identifies a >10 allele VNTR polymorphism with bands between 0.3 kb and 2.5 kb. RsaI, TaqI, MspI, PvuII, HaeIII and PstI also detect the polymorphism.
Frequency: 90% heterozygosity was observed with HinfI in 90 unrelated Caucasians.
Chromosomal Localization: The locus has been assigned to distal chromosome 1p by multipoint linkage analysis with loci known to span that region.
Mendelian Inheritance: Codominant segregation was observed in 45 three generation families.
Other Comments: RFLPs were observed under normal conditions of hybridization and washing.

TABLE 23
VNTR Clone pEFD126.3 on Chromosome 9q (D9S7)

Source/Description: A 4.2 kb BamHI fragment from cEFD126 isolated by the HBV-4 oligonucleotide was subcloned into the AccI site of pUC18.
Polymorphism: TaqI resolves a 5 allele VNTR polymorphism with alleles between 1.5-2.0 kb. BglII, MspI, PstI, PvuII and RsaI also detect the polymorphism.
Frequency: 71% heterozygosity was observed with TaqI in 111 unrelated Caucasians.
Chromosomal Localization: EFD126.3 has been assigned to distal chromosome 9q by multipoint linkage analysis with loci (ABO, ABL, AK1, ORM) known to span that region.
Mendelian Inheritance: Codominant segregation observed in 56 three generation families.
Other Comments: The probe was pre-associated with excess human DNA prior to hybridization. Otherwise, RFLPs were observed under normal hybridization and wash stringencies.

TABLE 24
VNTR Clone cCMM77

Source/Description: cCMM77 was obtained by screening with the myo-2 oligonucleotide.
Polymorphism: PstI identifies a >7 allele VNTR polymorphism. MspI, TaqI, RsaI, HindIII, EcoRI and PvuII also detect the polymorphism.
Frequency: The heterozygosity of the locus is 74%.
Other Comments: RFLPs observed under normal conditions.

TABLE 25
VNTR Clone oMCOB17 (D17)

Source/Description: cMCOB17 was obtained using an oligonucleotide configured to contain the nonamer consensus sequence.
Polymorphism: A 7 allele polymorphism was observed with HinfI. PstI reveals the polymorphism with bands between 1.2 kb and 2.1 kb.
Frequency: The locus show heterozygosity of 89%.
Chromosomal Localization: MCOB17 has been assigned to chromosome 17 by linkage analysis. The locus is linked to HtK9, THH59 and AC256.
Other Comments: RFLPs were observed under normal conditions.

TABLE 26
VNTR Clone cYNA4 on Chromosome 2 (D2S50)

Source/Description: The cosmid was isolated with YNH24-related oligonucleotide (GGAGCAGTGGGNNNTACA) from a human genomic library.
Polymorphism: MspI identifies a more than 10 allele VNTR polymorphism with a band between 2.0 and 5.0 kb. AluI, HaeIII, HinfI, TaqI, RsaI, BglII, PvuII and PstI also identify the polymorphism.
Frequency: The heterozygosity of the locus in 120 unrelated Caucasians is 85%.
Chromosomal Localization: YNA4 has been assigned to chromosome 2q, by multipoint linkage analysis with loci (CRYG, D2S3) known to span that region.
Mendelian Inheritance: Codominant segregation of the MspI RFLP was observed in 53 three generation families.
Other Comments: RFLPs were observed after competitive hybridization with total human DNA.

TABLE 27
VNTR Clone pMHZ10 on Chromosome 9q (D9S11)

Source/Description: A 3.8 kb PstI fragment from cMHZ10 isolated with the YNZ22 oligonucleotide was subcloned into the PstI site of pGEM4.
Polymorphism: MspI identifies a 5 allele VNTR polymorphism with alleles between 1.4-2.0 kb. EcoRI, HinfI, HindIII, PstI and PvuII also resolve the polymorphism. RsaI and TaqI do not adequately resolve the polymorphism.
Frequency: With MspI, 83% heterozygosity was observed in 72 unrelated Caucasians.
Chromosomal Localization: MHZ10 has been assigned to distal chromosome 9q by multipoint linkage analysis with loci (ABO, AK1, ABL) known to span that region.
Mendelian Inheritance: Codominant segregation of the MspI VNTR polymorphism was observed in 31 three generation families.
Other Comments: The probe was pre-associated with excess human DNA prior to hybridization. Otherwise, RFLPs were observed under normal hybridization and wash stringencies.

TABLE 28
VNTR Clone pMHZ13 on Chromosome 9q (D9S13)

Source/Description: A 3.3 kb PvuII fragment from cMHZ13 isolated by the YNZ22 oligonucleotide was subcloned into the HincII site of pGEM4.
Polymorphism: PstI identifies an 8 allele VNTR polymorphism with alleles between 1.6–2.3 kb. HindIII, RsaI and TaqI also resolve the polymorphism. MspI does not adequately resolve the polymorphism.
Frequency: 78% heterozygosity was observed with PstI in 72 unrelated Caucasians.
Chromosomal Localization: MHZ13 has been assigned to chromosome 9q by multipoint linkage analysis with loci (ABO, AK1, ABL) known to span that region.
Mendelian Inheritance: Codominant segregation of the PstI VNTR polymorphism was observed in 31 three generation families.
Other Comments: The probe was pre-associated with excess human DNA prior to hybridization. Otherwise, RFLPs were observed under normal hybridization and wash stringencies.

TABLE 29
VNTR Clone cTB07 (D10S28)

Source/Description: Obtained from a somatic cell hybrid which contained human chromosomes 10 and Y. Hybrid DNA was digested partially with Sau3AI and inserted into the BamHI site of pWE15.
Polymorphism: MspI identifies a >20 allele VNTR locus with bands between 2 kb and 7 kb. TaqI, RsaI, BglII, PstI and PvuII also detect the polymorphism.
Frequency: 96% heterozygosity was observed in 61 unrelated Caucasians.
Chromosomal Localization: Assigned to chromosome 10p by linkage analysis.
Mendelian Inheritance: Codominant segregation of RFLP was observed in 32 three generation families.
Other Comments: RFLPs were observed after competitive hybridization with total human DNA.

TABLE 30
VNTR Clone cKKA39 on Chromosome 14 (D14S23)

Source/Description: cKKA39 was isolated from a human genomic cosmid library by an oligonucleotide (GGGTGGGGTGGGNNNNNG) configured after the consensus.
Polymorphism: MspI identifies a more than 10 allele VNTR polymorphism with a band between 2.0 and 4.0 kb. HinfI, HaeIII, AluI, TaqI, RsaI, PstI, PvuII and BglII also show the polymorphism.
Frequency: The heterozygosity of the locus is 83% in 20 unrelated Caucasians.
Chromosomal Localization: KKA39 has been assigned to distal chromosome 14q by multipoint linkage analysis with loci (D14SI, GM, PI) known to span that region.
Mendelian Inheritance: Codominant segregation of the RFLP was observed in 50 three generation families.
Other Comments: RFLPs were observed under total human DNA prehybridization and hybridization.

TABLE 31
VNTR Clone pYNZ21 on Chromosome 19 (D19)

Source/Description: A 2.4 kb MspI fragment obtained by the zeta-globin oligonucleotide cloned into the AccI site of pUC18.
Polymorphism: MspI identifies a >10 allele polymorphism with a band between 0.8 kb and 3.2 kb. TaqI, AluI and HinfI also detect the polymorphism. Not polymorphic for RsaI.
Frequency: 77% heterozygosity among 120 American

TABLE 31-continued
VNTR Clone pYNZ21 on Chromosome 19 (D19)

Caucasians.
Chromosomal Localization: YNZ21 shows linkage with D19S20 and D19S21 on 19p.
Mendelian Inheritance: Codominant segregation observed in 60 families.
Other Comments: RFLPs were observed under normal assay conditions. Although YNZ21 is mapped to chromosome 19, the gene symbol is not yet designated.

TABLE 32
VNTR Clone pTHH33 on Chromosome 1q (D1S81)

Source/Description: A 5.6 kb EcoRI fragment from cTHH33 isolated with HBV-2 oligonucleotide was subcloned into the EcoRI site of pUC18.
Polymorphism: RsaI identifies a >10 allele VNTR polymorphism with bands between 4.0 kb and 6.5 kb. TaqI, BglII, PstI, PvuII, BamHI, EcoRI, MspI and HindIII also detect the polymorphism.
Frequency: 85% heterozygosity was observed with RsaI in 82 unrelated Caucasians.
Chromosomal Localization: The locus has been assigned to distal chromosome 1q by multipoint linkage analysis with loci known to span that region.
Mendelian Inheritance: Codominant segregation was observed in 41 three generation families.
Other Comments: RFLPs were observed under normal conditions of hybridization and washing.

TABLE 33
VNTR Clone pTHH59 on Chromosome 17q (D17S4)

Source/Description: A 3.8 kb PstI fragment from cTHH59 identified by the HBV-1 oligonucleotide was subcloned into the PstI site of pBR322.
Polymorphism: PvuII resolves a 6 allele VNTR polymorphism with bands between 0.8 kb and 1.8 kb. TaqI resolves the system almost as well with alleles between 3.0–4.0 kb. RsaI, PstI and EcoRI also detect the polymorphism. Not polymorphic for BglII.
Frequency: 76% heterozygosity was observed with PvuII in 100 unrelated Caucasians.
Chromosomal Localization: The locus was assigned to chromosome 17 by somatic cell hybrid analysis and to 17q by multipoint linkage analysis to a locus (TK1) known to be in that region of chromosome 17.
Mendelian Inheritance: Codominant segregation of the VNTR polymorphism has been observed in 50 three generation families.
Other Comments: RFLPs were observed under normal hybridization conditions.

TABLE 34
VNTR Clone cMLJ205

Source/Description: cMLJ205 was obtained using the myo-1 oligonucleotide.
Polymorphism: A greater than 10 allele polymorphism is observed with MspI-digested genomic DNA. The bands range from 1.5 to 4.5 kb.
Frequency: The heterozygosity of the locus is 83%.
Other Comments: RFLPs observed under normal conditions.

TABLE 35
MCT Series of VNTR Clones

Source/Description: cMCT4, cMCT14, cMCT15, cMCT32, cMCT96, cMCT103, cMC5105, cMCT113, cMCT117, cMCT127, cMCT129, cMCT136, cMCT144 and cMCT164 were obtained using an oligo containing alternating G

TABLE 35-continued
MCT Series of VNTR Clones and T residues.

Frequency: Each of the clones showed a high level of heterozygosity at the respective locus.

Other Comments: RFLPs observed under standard conditions. The clones of the MCT series hybridize to loci containing alleles that are generally less than 2 kb in size.

In the library screening procedures used herein and generally with any screening, it is not uncommon to obtain clones with substantial sequence homology. A library is prepared from the DNA of more than one cell or chromosome and some sequences may be under-represented or over-represented in the bank because of chance, physical characteristics of sequences themselves, etc. (We mentioned earlier of the apparent paucity of VNTR clones in the phage library maintained in a host recA+ host and the abundance of VNTR clones in the cosmid library maintained in a recA− host.) The result is that clones may be exact duplicates, may be very similar except for one to a minority of base changes or they may overlap. Clones with substantial sequence homology that are derived from a single locus can be identified by filter hybridization of the clones to each other, comparing sequence data, comparing map locations, finding cosegregation of the clone sequences in multigeneration families, etc. Several clones were found to have substantial sequence homology and in fact identify the same locus, for example, both pCMM73 and pCMM86 map to D17S74 and pMLJ14 cosegregates with pCMM101.

It will be appreciated that the range of oligos need not be restricted to sequences related to the consensus sequences of VNTR loci near insulin, zeta-globin, or myoglobin or related to HB virus. Consensus sequences from first generation clones can be used as probe for obtaining additional clones from a library. For example, cYNA13 and cYNA4 were obtained by screening with an oligo based on the consensus of pYNH24; and pMHZ10, pMHZ13 and pMHZ47 were obtained with an oligo based on the consensus of pYNZ22. In fact, any oligo with substantial sequence homology to the consensus sequence can be used for library screening. pMCT118 was obtained by screening with a 20mer comprised of alternating G and T residues. cKKA39 was obtained by screening with an 18mer having about 50% homology with the YNH24 18mer.

It will be further appreciated by artisans skilled in cloning and gene mapping that different clones can detect polymorphism at a single locus. For example, if a pair of EcoRI sites define a 7kb fragment that contains directly in the center of that fragment 1kb of tandem repeats, there are 3kb of sequences that flank the repeats on each side. If those flanking sequences could be used as probe to detect the same polymorphism when genomic DNA is digested with EcoRI. Table 35 presents the characterized clones of the invention and the gene locus from which the clone originated. The restriction fragment noted in the table represents the largest allele observed to date. The choice of enzyme and size of fragment are not meant to be limiting because restriction sites may be situated asymmetrically about the repeats or other restriction enzymes with sites flanking each locus that yield larger fragments may be found.

TABLE 36
Restriction Fragment Containing VNTR Sequence

| Clone | Locus | Restriction Enzyme | Fragment Size(kb) |
|---|---|---|---|
| pYNH24 | D2S44 | PvuII | 13 |
| pCMM101 | D14S13 | HinfI | 9.5 |
| pYNZ22 | D17S30 | TaqI | 3.3 |
| cEFD64 | D3S42/S46 | HinfI | 5.5 |
| pJCZ3.1 | D19S20 | BamHI | 6 |
| cYNA13 | D1S74 | AluI | 13 |
| pCMM86 | D17S74 | TaqI | 8.5 |
| pEKMDA2I | D16S83 | AluI | 25 |
| pJCZ16.2 | D17S30 | TaqI | 3.3 |
| pJCZ67 | D7S396 | EcoRI | 9 |
| cMHZ47 | D13S52 | TaqI | 4 |
| pMLJ14 | D14S13 | PstI | 16.5 |
| pCMM6 | D20S19 | TaqI | 6 |
| pCMM66 | D14S22 | PstI | 6 |
| pCMI327 | D17 | PvuII | 4 |
| cEFD52 | D17S26 | pVuII | 10 |
| pEFD139 | D22 | PstI | 8 |
| pRMU3 | D17S24 | TaqI | 3.8 |
| pMCT118 | D1S80 | HinfI | 2.5 |
| pEFD126.3 | D9S7 | TaqI | 2 |
| cCMM77 | | PstI | 6 |
| pCMOB17 | D17 | PvuII | 4 |
| cYNA4 | D2S50 | HaeIII | 6 |
| pMHZ10 | D9S11 | MspI | 2 |
| pMHZ13 | D9S13 | PstI | 2.3 |
| cTBQ7 | D10S28 | TaqI | 7 |
| cKKA39 | D14S23 | RsaI | 5.5 |
| pYNZ21 | D19 | MspI | 3.2 |
| pTHH33 | D1S81 | RsaI | 6.5 |
| pTHH59 | D17S4 | TaqI | 4 |
| cMLJ205 | | MspI | 4.5 |

Accordingly, any unique sequence contained within the 13kb PvuII fragment that carries the D2S44 locus recognized by pYNH24 could serve as probe to that locus, including nucleic acids carrying D2S44 VNTR consensus sequences or carrying sequences that fall between D2S44 and a PvuII restriction site. It will be apparent to the artisan that not all sequences will find ubiquitous use. Thus, a unique sequence clone of the 13kb PvuII fragment that is 12kb from D2S44 may detect polymorphism if the genomic DNA is digested with PvuII but will not detect the polymorphism if the genomic DNA is digested with MspI which yields VNTR-containing fragments 4kb or less in size.

Although clones of the repeats themselves are preferred over single copy flanking probes because of favorable hybridization kinetics, single copy flanking clones can be as advantageous as repeat clones by combining with methods of amplification. A preferred method of amplification is the polymerase chain reaction (PCR) (Saiki et al. *Science* (1985) 230, 1350). The PCR amplifies in vitro defined nucleic acid fragments. Thus, smaller amounts of DNA are required or in this case, the signal from a PCR-amplified flanking unique sequence can be obtained following hybridization as distinctly and quickly as that obtained when using nucleic acid fragments that hybridize to the repeats. Briefly, the procedure requires the base sequence of a flanking fragment and synthesis of oligonucleotides complementary to sequences on opposite strands up to 2000 base pairs apart. The amplification occurs in oligonucleotide excess by repeated cycles of denaturation-hybridization-synthesis. The nucleic acid fragment amplified is delimited by the sequences to which the oligos hybridize. Mullis & Faloona, *Meth Enz* (1987) 155, 335.

A further advantage of the VNTR clones described herein is obtained by combining the method of the PCR using loci that with selected restriction enzymes yield alleles no more than 2000bp in length and preferably no more than 1000bp in length. The PCR works well for amplifying smaller fragments of DNA. Thus, oligonucleotides are configured after unique sequences immediately flanking on each side of the cluster of repeats and allelic differences can be revealed absent hybridization. With locus-specific oligos and sufficient amplification, bands are revealed on ethidium bromide-stained gels following electrophoretic separation. Under appropriate conditions, genetic identification of an individual by this method is obtained within a day of DNA extraction.

Whereas the PCR enhances sensitivity by amplifying target DNA in vitro, an alternative strategy is to enhance signal by concentrating more label at the target site. That can be achieved for example by attaching multiple reporter molecules to the clone; by using multiple labeled clones to a target sequence; by combining those approaches, namely, multiple reporter molecules on multiple clones to a target sequence; by employing labeled secondary clones specific to unique sequences fashioned to the primary clone that hybridizes to a target sequence (Dunn & Hassell, *Cell* (1977) 12, 23); or amplification of hybridized clones particularly recombinant RNAs that serve as templates for $Q\beta$ replicase (Chu et al., *Nucl Acid Res* (1986) 14, 5591).

In the indirect or sandwich assay of Dunn & Hassell, a bifunctional clone is produced, for example containing YNH24 sequences and SV40 sequences. The clone is hybridized to genomic DNA and bound molecules visualized following a subsequent hybridization with highly labeled SV40 clones. The labeled clones can themselves serve as substrate. This would in effect result in a network of hybridized sequences each carrying one or more reporter molecules.

The $Q\beta$ replicase system relies on the prolific autocatalytic capability of the RNA-directed RNA polymerase, $Q\beta$ replicase, to synthesize in an exponential reaction mechanism a large number of product RNA fragments from a small number of template strands. Million-fold increases of RNA are not uncommon. Foreign sequences that are inserted into a $Q\beta$ replicon enable hybridization to genomic target sequences. Then the replicon is amplified in the RNA polymerase reaction and the product RNAs are visualized. (Lizardi et al., *Biotech* (1988) 6, 1197).

In order to accomplish the identification of individuals or tissue samples within the scope of the present invention, one or more loci of interest are analyzed using standard filter hybridization technologies. As was discussed previously, a VNTR locus having multiple alleles which occur frequently in the population is preferred.

In order to initiate the testing procedure, a tissue sample is obtained. It will be appreciated that the sample may comprise any type of tissue. For most applications, it is likely that blood would be the tissue of choice. This would be true in the case of paternity testing and the like. However, other tissues, including skin, semen, hair and other body fluids or tissues may be acceptable for specific purposes. Using the method of the present invention no more than approximately 10 ul of blood is required in order to perform the testing procedure. DNA can be obtained from any nucleated cell that is live, dead or preserved.

The testing procedure essentially requires that the cells in the tissue sample be lysed and that the DNA obtained from the lysed cells be isolated and cleaved with a restriction enzyme. It should be appreciated that because the variability at a VNTR locus arises from copy number differences of tandem repeats, any restriction endonuclease with sites flanking the repeats will reveal the polymorphism. The enzymes noted in the specification are representative and are non-limiting examples of enzymes which can be used for a VNTR clone. In a preferred embodiment, restriction enzymes with sites very close to the cluster of repeats are desired. The result is smaller restriction fragments which are easier to discriminate on agarose gels. The DNA is then applied to gel and electrophoresed using widely known and generally accepted procedures. The DNA is then denatured such that it exists in the single strand form.

At this point, the DNA is transferred to a membrane according to the technique of Southern (*J Mol Biol* (1975) 98, 503) which is widely practiced and accepted in the art. Alternatively, a PCR, $Q\beta$ replicase or other amplification procedure as discussed above could be utilized.

The DNA thus isolated and denatured is hybridized with one or more VNTR clones of the type described above. Several such clones will be discussed in additional detail below. Following wash, the location of the labeled nucleic acid fragment is determined using techniques such as an autoradiogram of the membrane filter. It will be appreciated that while radiolabeling of the clone is emphasized herein, labeling by other methods is acceptable. Labeling with fluorescent dyes or with biotinylated nucleotides, for example, has worked as well as radiolabeled probes. It is only necessary that the location of the hybridized clone be determinable.

The specific location of the hybridized duplex provides information concerning the particular characteristics of the DNA. This can be seen by the autoradiograms which comprise FIGS. 1 through 6 herein which are described in additional detail below. By employing multiple clones for multiple VNTR loci, it is possible to provide a very accurate genetic identification of an individual from which the tissue samples were obtained. Thus, it is possible to compare the results with that individual or with possible parents or offspring of the individual to identify, not only the individual, but the paternity of the individual.

The present invention can determine paternity with virtual certainty. Multiple clones of multiple VNTR loci can be employed. Each locus chosen will have multiple alleles occurring at high frequency in the population. Thus, by employing a plurality of clones, the possibility of two individuals producing the same data becomes essentially zero.

The same technique is employed when it is desired to link a tissue sample with a specific individual. For example, if a sample of tissue or body fluid is found at a crime scene using the present invention, that sample can be tied precisely to a particular individual.

Similarly, in the case of bone marrow transplants it is desirable to determine whether an individual's cancerous cells have begun to regenerate. Thus, cells are removed and analyzed according to the present invention. If the results from the bone marrow match those from the patient, it is possible that cancerous cells are reappearing. Similarly, if the results from the bone marrow do not match the recipient, it is clear that only transplanted cells exist.

Numerous other application are also possible, some of which have been discussed above. These may include, for example, determining monozygosity versus dizygosity in twins, identifying potential organ donors, forensic applications, identification of diseased genes, and mapping of the genome.

EXAMPLES

The following examples illustrate aspects of the present invention. In the examples, standard procedures such as those described in Maniatis et al., supra; *Meth Enz.* supra: Wyman & White, supra: and Litt & White, supra were followed.

EXAMPLE 1

Oligonucleotides were synthesized according to the sequence of genes known to behave as VNTR loci linked to insulin, zeta-globin, or myoglobin), or with sufficient sequence homology to behave potentially as VNTR loci. End-labeling of the oligos was carried out according to standard procedures.

One to two genome equivalents (i.e., 75,000–150,000) of a cosmid library were plated out and transferred to nylon filters. Hybridization buffer contained 5×SSC, 0.05M Tris-HCl, at pH 7.4, 1× Denhardt's solution and 0.01 mg/ml yeast tRNA. The sequence and assay conditions for each oligo were those listed in Table 1.

Three hundred seventy-two cosmids ascertained by the oligonucleotides were tested for polymorphism using genomic DNAs of 6 unrelated individuals. Samples were digested initially with any of a variety of restriction endonucleases, including MspI, TaqI, RsaI, BamHI, BglII, PstI, EcoRI, HindIII, PvuII, HinfI, HaeIII and AluI. The goal was to identify the restriction enzyme that revealed the largest number of alleles as well as the smallest, and therefore most precisely resolved, DNA fragments. Restriction enzyme digests, agarose gel electrophoresis, DNA blotting to nylon membrane, radiolabeling of VNTR clones, and filter hybridization assays were carried out according to standard protocols. FIG. 1 sets forth a reproduction of autoradiographs of representative data. The photographs illustrate patterns typical of a VNTR locus as revealed by hybridization with an entire cosmid.

EXAMPLE 2

Figure 2:
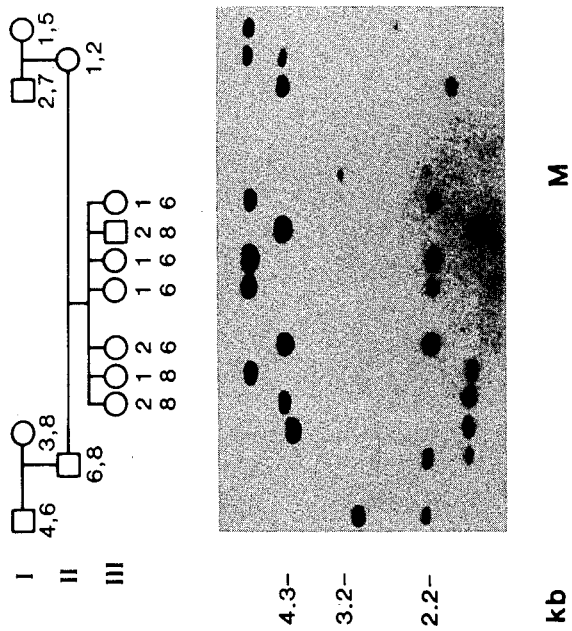
FIG. 2 comprises an autoradiogram together with pedigree showing the results of a screening.

The segregation of VNTR alleles at the YNH24 (D2S44) locus in a three generation family is represented in FIG. 2. DNA samples prepared from peripheral blood were done according to standard procedures. Restriction digests were done with MspI. Three micrograms of each digest were loaded per lane and the fragments separated. Conventional autoradiography revealed the alleles detected by the clone. The pattern was consistent with segregation of a codominant trait with 8 alleles present in that family.

Example 2 demonstrates the Mendelian inheritance of the gene detected by pYNH24. The alleles, and therefore the chromosome regions within which they are imbedded, can be followed unambiguously through the family. For example, the maternal grandmother is heterozygous at the YNH24 locus having alleles 1 and 5. Allele 1 is inherited by her daughter, who passes it onto four of her children. It will be appreciated that if there were a dominant disease gene linked tightly with the YNH24 locus, the disease would be expressed in each of those individuals.

EXAMPLE 3

Figure 3A:
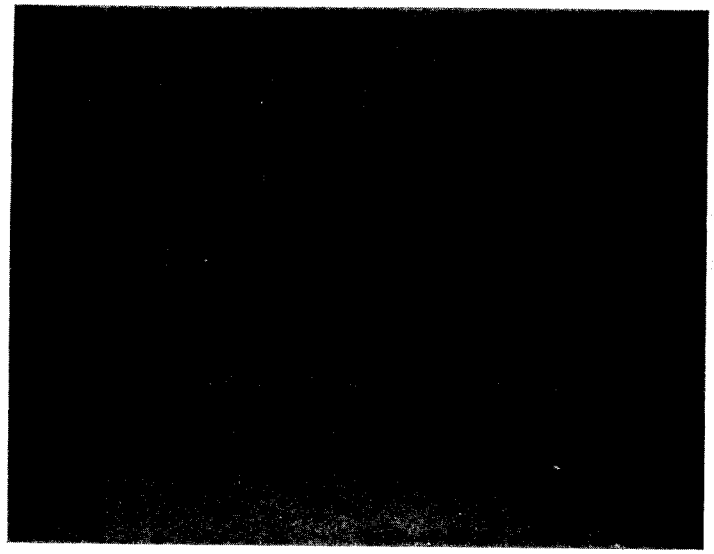
FIG. 3 comprises a pair of autoradiograms showing the results of analyzing whether detected loci are multiallelic. The lanes contain DNA from unrelated individuals. pJCZ16.2 and cEFD52 were used. See Example 3 for details.
Figure 3B:
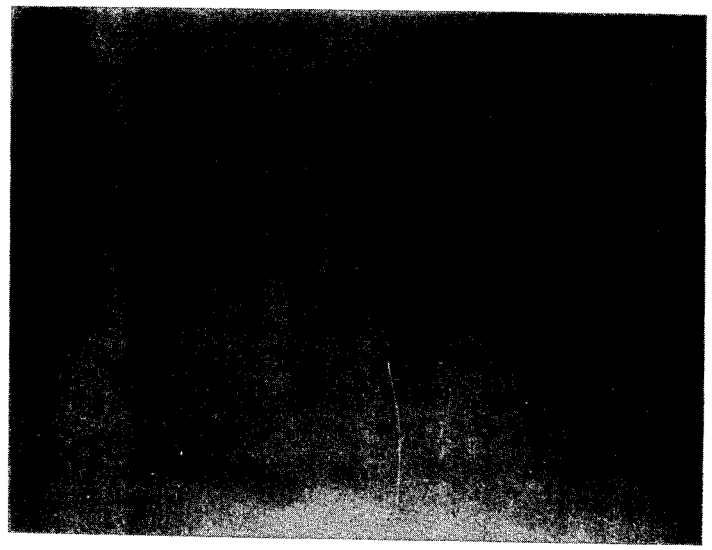

Example 3 depicts the characterization of allele frequency of selected VNTR loci. Clones that detected large numbers of alleles in the preliminary survey were retested with other restriction enzymes. DNA samples from unrelated individuals were cleaved according to manufacturers' recommendations. The digested DNA samples were electrophoresed on agarose gels and transferred to nylon membrane. FIG. 3 includes autoradiograms which represent data related to JCZ16.2 and EFD52. The data show clearly that VNTR loci identified by those clones carry multiple alleles. Accordingly, the multiple allelic VNTR locus identified can be useful in genetic identification and paternity testing.

EXAMPLE 4

Example 4 demonstrates how paternity can be determined using VNTR loci. Initially, the paternity index and probability of paternity are determined. X equals the chance an alleged father could be the biological father of a child. Y equals the chance a random person could be the biological father of the child. The resulting paternity index (PI=X/Y) is a measure of the likelihood that the alleged father is the biological father. The Bayesian probability of paternity includes an a priori probability which is usually 0.5. Thus, the formula is modified to read $PI = 1/(1+Y/X)$. (It is assumed that the mother is the biological mother).

In the present example, a mother, child, and two putative fathers were screened using VNTR clones of the present invention. In particular, pYNH24, pYNZ22, pCMM101, pJCZ3.1, and pEKMDA2I were used. The data obtained using those clones are summarized below. (The X and Y values are calculated based on Mendelian inheritance of the alleles. The alleles are numbered for identification, thus, the mother was heterozygous for alleles 33 and 86 at the YNH24 locus.)

|  | Mother | | Child | | Father 1 | | Father 2 | | X | Y |
|---|---|---|---|---|---|---|---|---|---|---|
| YNH24 | 33 | 86 | 33 | 35 | 35 | 35 | 25 | 42 | 1.0 | 0.0331 |
| YNZ22 | 4 | 9 | 4 | 3 | 3 | 3 | 5 | 9 | 1.0 | 0.169 |
| CMM101 | 9 | 28 | 9 | 4 | 4 | 20 | 22 | 28 | 0.5 | 0.027 |
| JCZ3.1 | 16 | 12 | 16 | 9 | 9 | 9 | 16 | 16 | 1.0 | 0.292 |
| EKMDA2I | 4 | 8 | 4 | 4 | 4 | 9 | 8 | 10 | 0.5 | 0.023 |
|  |  |  |  |  |  | Cumulative Value | | | 0.25 | 1.01 × $10^{-6}$ |

It is evident that Father 1 is determined, of virtual certainty, to be the father of the child. The alleles in the left-hand column for the child were inherited form the mother. Each of the alleles in the right-hand column were inherited from the child's father. Thus, for YNH24, the child inherited 33 from the mother and 35 from the father. Father 1 is homozygous for 35 and father 2 carries 2 different alleles at that locus.

Applying the calculations set forth above, the paternity index is $X/Y=2.46 \times 10^5$. The probability of paternity is therefore 99.9996%. The probability that Father 2 is the actual father is virtually zero.

Accordingly, it will be appreciated that the present invention provides the capability of accurate and precise paternity identification.

EXAMPLE 5

VNTR clones were used to determine whether a suspect in a rape case could indeed have been the alleged rapist.

Upon investigation of a rape, a sample of semen and a sample of hair were recovered. Later, a suspect was arrested. The hair, semen, and a sample of blood were screened according to the protocols described herein. Clones pMLJ14, pYNH24, pCMM101, and pJCZ3.1 were employed. The results from the screening are presented in the following chart with the numbers corresponding to particular alleles revealed by the DNA clones.

|  | Hair |  | Semen |  | Suspect |  |
| --- | --- | --- | --- | --- | --- | --- |
| MLJ14 | 26 | 7 | 1 | 29 | 1 | 29 |
| YNH24 | 10 | 14 | 22 | 31 | 22 | 31 |
| CMM101 | 18 | 11 | 24 | 5 | 24 | 5 |
| JCZ3.1 | 5 | 15 | 11 | 16 | 11 | 16 |

Based on the results of the above test, it is possible to conclude that the semen sample originated with the suspect, whereas the hair did not. It can be seen that each allele of the semen sample matched the blood sample of the suspect whereas none of the alleles from the hair sample matched the suspect. Accordingly, it can be determined that the suspect is indeed the rapist.

Thus, it will be appreciated that the present invention provides clones and methods for use in forensic applications.

EXAMPLE 6

It is desirable to determine whether cancerous cells have regenerated in the marrow of a bone marrow transplant recipient. VNTR clones are useful in that respect.

In order to make the determination, a blood sample and marrow sample were acquired. DNA of the two samples were screened using clones pEKMDA2I, cEFD64, cYNA13, and pCMM101. The following results were obtained.

|  | Recipient |  | Marrow |  |
| --- | --- | --- | --- | --- |
| EKMDA2I | 8 | 12 | 16 | 12 |
| EFD64.2 | 5 | 17 | 10 | 5 |
| YNA13 | 5 | 4 | 2 | 17 |
| CMM101 | 25 | 11 | 2 | 22 |

It can be concluded from the results that there has been no significant regeneration of the cancerous cells in the bone marrow.

EXAMPLE 7

Figure 4:
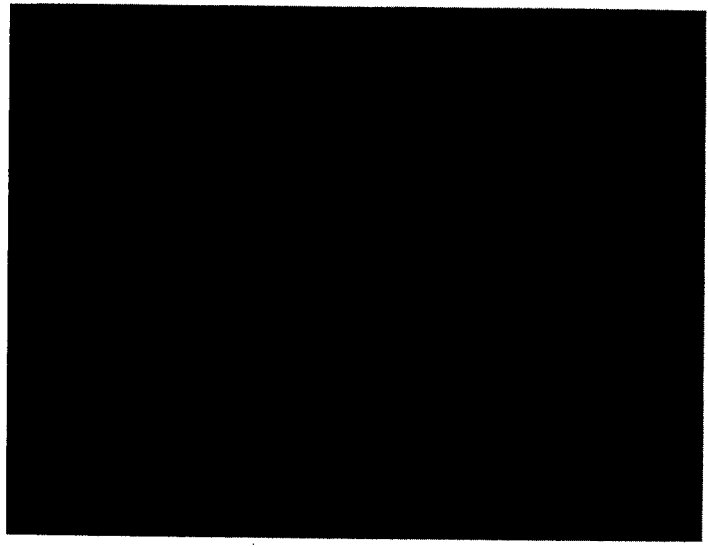
FIG. 4 is an autoradiogram showing the results of paternity testing using pJCZ3.1 and HinfI-digested DNA. The central three lanes containing two bands each are from left to right samples of the mother, fetus and purported father.

Paternity testing was done using clone pJCZ3.1 and restriction enzyme HinfI. Samples of DNA were obtained from the mother, fetus and purported father. The result of the paternity test is illustrated in FIG. 4. In the left lane is the result from analysis of the mother's DNA, in the middle lane is the result of the analysis of the fetus, and in the right lane is the result of the analysis of the father. It can be seen from FIG. 4 that VNTR alleles from the mother and father were inherited by the fetus.

EXAMPLE 8

Figure 5:
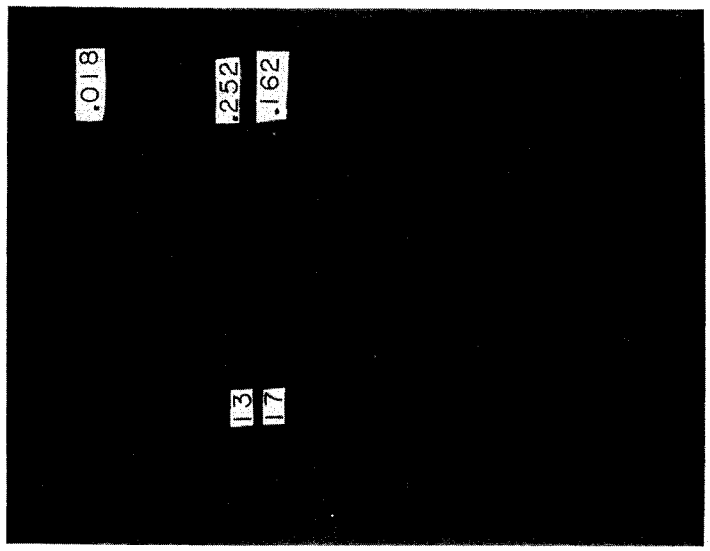
FIG. 5 is an autoradiogram showing the results of paternity testing using pJCZ16.2 and HinfI-digested DNA. The central three lanes are from left to right samples from the mother, fetus and purported father. The probe-enzyme combination detected in the applicant's laboratory and the numbers 0.018, 0.252 and 0.162 refer to frequency of the corresponding allele.

Paternity testing was done using clone pJCZ16.2 and restriction enzyme HinfI. Samples of DNA were obtained from the mother, fetus, and purported father. The result of the paternity test is illustrated in FIG. 5. In the left lane is the result from analysis of the mother's DNA, in the middle lane is the result of the analysis of the fetus, and in the right lane is the result of the analysis from the father. It can be seen from FIG. 5 that VNTR alleles from both the mother and father were inherited by the fetus.

EXAMPLE 9

Figure 6:
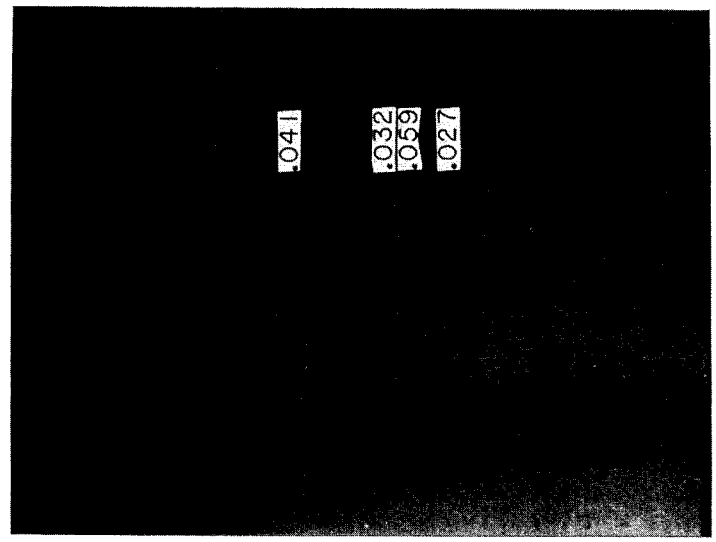
FIG. 6 is an autoradiogram showing the results of paternity testing using pYNH24 and AluI-digested DNA. From left to right the lanes contain molecular weight markers, DNA of the mother, DNA of the fetus and DNA of the purported father. The numbers 0.041, 0.032, 0.059 and 0.027 refer to frequencies of the corresponding alleles.

Paternity testing was done using clone pYNH24 and the restriction enzyme AluI. Samples of DNA were obtained form the mother, fetus, and the purported father. The result of the paternity test is illustrated in FIG. 6. In the left lane is the result from analysis of the mother's DNA, in the middle lane is the result of the analysis of the fetus, and in the right lane is the result of the analysis of the father. It can be seen from FIG. 6 that VNTR alleles from both the mother and father were inherited by the fetus.

EXAMPLE 10

A flanking clone not containing the tandem repeats can detect a VNTR locus if the restriction fragment contains the unique flanking sequence and the cluster of repeats. pCMM101 and pCMM66 originated from the same cosmid. pMLJ14 originated from another cosmid. Mapping data revealed that the three clones are syntenic with chromosome 14 and in fact the clones cosegregated in three generation families. Subsequent restriction mapping and sequencing of the clones revealed identity of pCMM101 and pMLJ14. The inserts of those clones carry repeat sequences. pCMM66, however does not carry repeat sequences and arose from a region flanking the cluster of tandem repeats. Whereas pCMM101 and pMLJ14 detect the polymorphism in MspI-digested genomic DNA, pCMM66 does not. The reason is the flanking sequence recognized by pCMM66 falls outside the smaller MspI VNTR-containing fragments.

EXAMPLE 11

Figure 7:
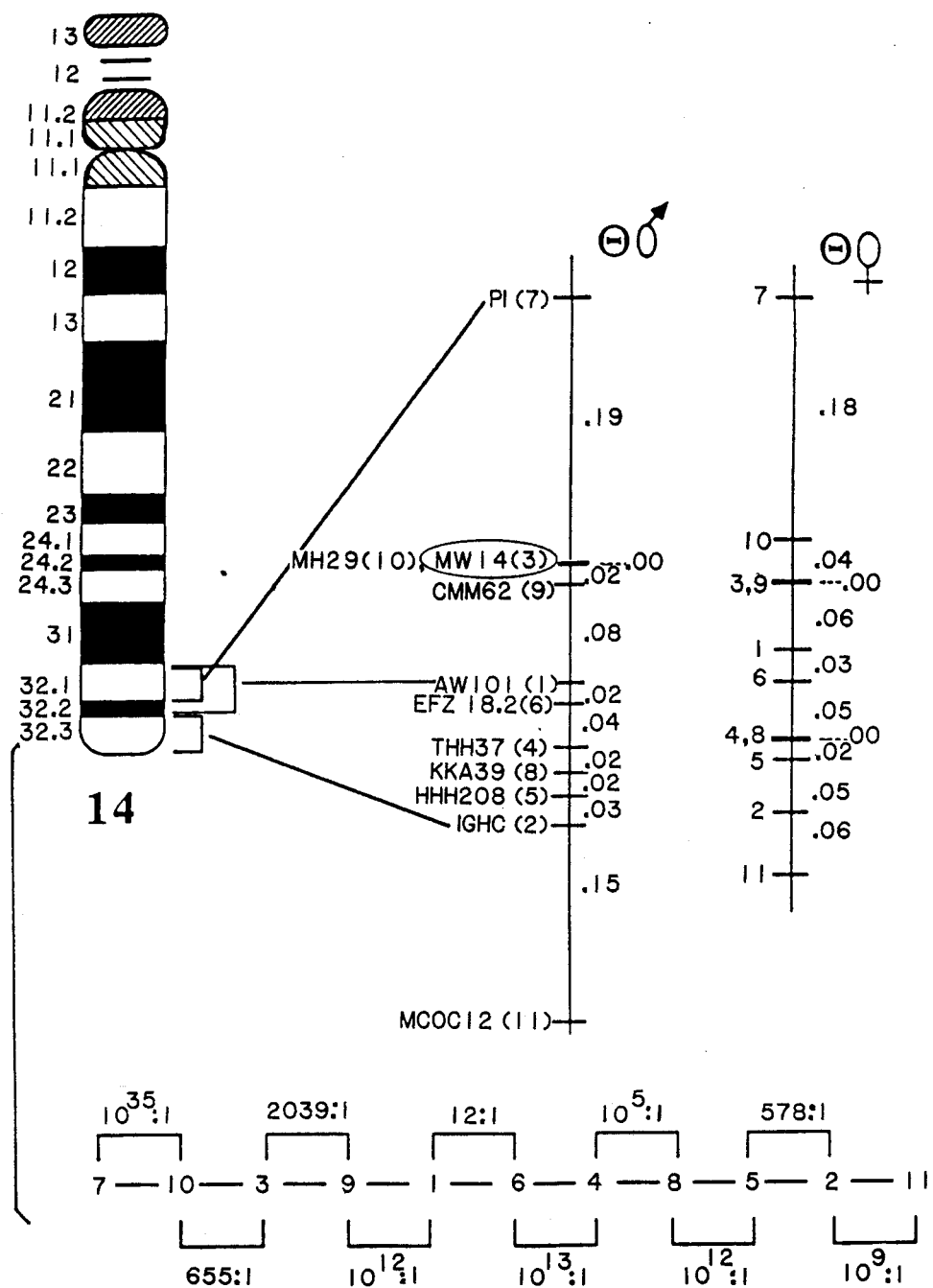
FIG. 7 comprises an ideogram and linkage maps of human chromosome 14. The genes PI and MCOC12 delimit that region which likely contains more genes than presented in the figure. D14S22, which is defined by pMLJ14, is 19cM from PI and 2cM from CMM62. At the bottom is a diagram showing the most likely gene order as determined from segregation analysis of those genes in varying combinations within families. The ratios bridging adjacent genes represent the odds that the presented gene order is real.

An ideogram and sex-specific linkage maps of HSA14 (human chromosome 14) are depicted in FIG. 7. Ten genes were mapped by a combination of techniques to 14q32.1-tel. The genes PI and MCOC12 delimit that region which likely contains more genes than presented in the figure. The relative distances between the genes are related to the likelihood of crossover between the genes. The closer the genes the less likely a crossover between those genes. D14S22, which is defined by pMLJ14, is 19cM from PI and 2cM from CMM62. At the bottom is a diagram showing the most likely gene order as determined from segregation analysis of those genes in varying combinations within families. The ratios bridging adjacent genes represent the odds that the presented gene order is real.

EXAMPLE 12

Figure 8:
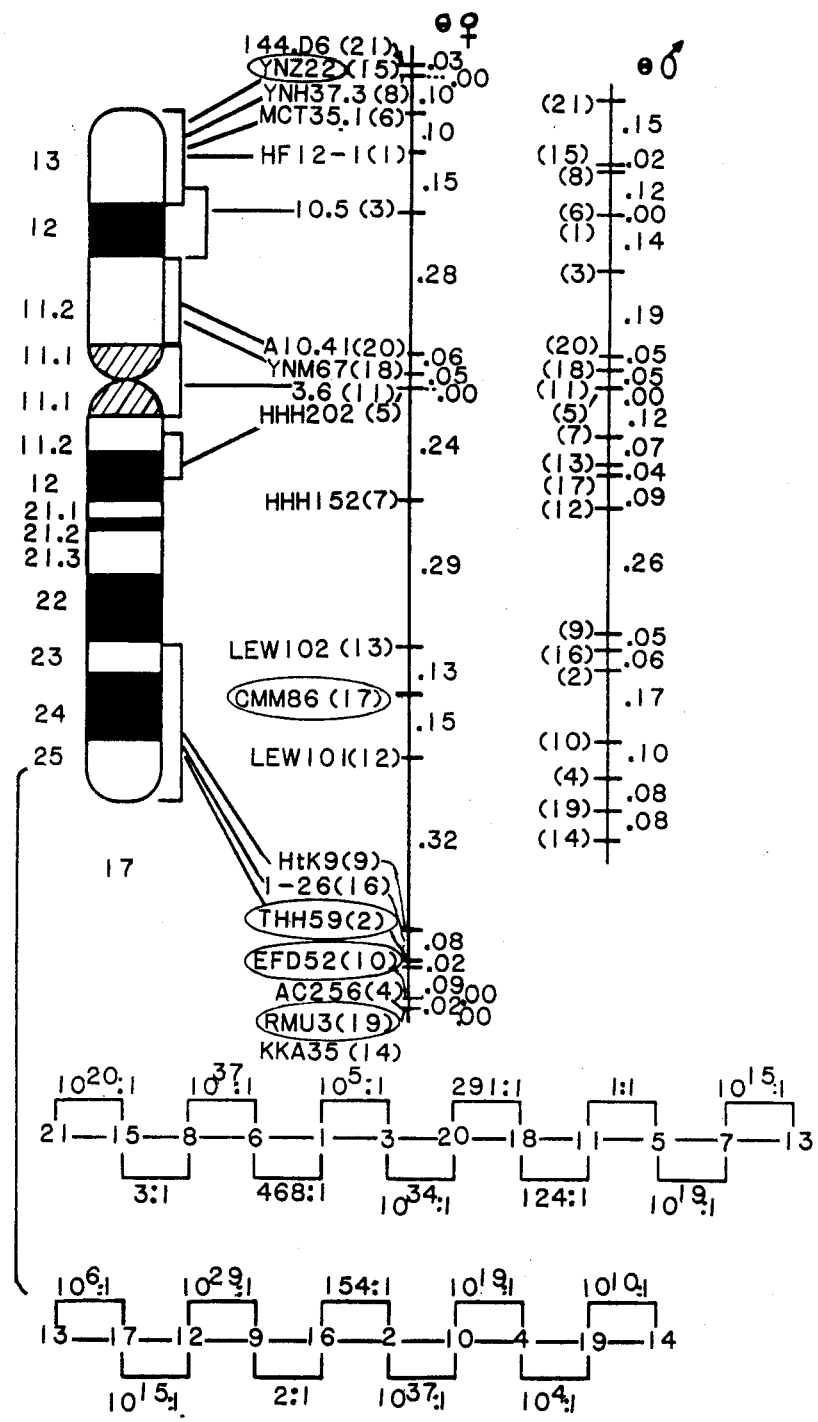
FIG. 8 comprises an ideogram and linkage maps of human chromosome 17. 144-D6(21) maps to 17p13, 3.6(11) maps to the centromeric region and KKA35(14) maps near the telomere of 17q. At the bottom is a diagram showing the most likely gene order as determined from segregatioln analysis of those genes in varying combinations within families. The ratios bridging adjacent genes represent the odds that the presented gene order is real.

An ideogram and sex-specific linkage maps of HSA17 are depicted in FIG. 8. In this case, the gene loci are not restricted to a specific region but instead are dispersed along the length of the chromosome. Thus, 144-D6(21) maps to 17p13, 3.6(11) maps to the centromeric region and KKA35(14) maps near the telomere of 17q. Five VNTR loci map to chromosome 17 - D17S30 (YNZ22), D17S74 (CMM86), D17S4 (THH59), D17S26 (EFD52) and D1724 (RMU3).

EXAMPLE 13

A partial base sequence of a CMM101 allele has been obtained by producing a series of DNase I deletion fragments and sequencing the opposite strands by the chain termination method of Sanger et al., supra. The following is a sequence from one of the fragments: polylinker—TC TCCACCTCAGCNNC TCCACCTCAGCCCCC TCCACCTCAGCCCCC TC TCCACCTCAGCCGNC TCCACCTCAGCCCCC NC TCCACCTCAGCCGCC TCCACCTCAG.... The repeat units are underlined and set off by spaces. Note that the unit contains 14 or 15 bases and that some monomers contain an additional dinucleotide. The consensus of the complementary strand inferred from the fragment noted above and other fragments is 5'-GGGGGCTGAGGTGGA-3'.

EXAMPLE 14

A partial base sequence of an EFD126.3 allele is as follows: flanking-GACCAAGGGGAAGA AGTCAAGTTGGGGGA GACCAAGGGGAAGA GGTTGGGGTGGGGA GACCAAGGGGAAGA GGTGTTTGTGGGGA GACCAAGGGGAAGA GGCNTGGGGGTGGA.... The repeat at that locus is a 28–30bp unit with an apparent hierarchic order. Each unit is itself comprised of two units, a conserved 14bp region, delimited by spaces above, and a divergent 14–16bp region, delimited by spaces and underlined above. An example of the conserved region of one of the units is: 5'-GACCAAGGGGAAGA. The adjacent divergent region of that unit is GGTTGGGGTGGGGA-3.

SUMMARY

Most of the VNTR clones that fall within the scope of the present invention have been isolated from cosmid libraries by hybridization with particular oligonucleotide probes. Examples of the oligonucleotides include those based on the consensus sequences of VNTR loci near zeta-globin, myoglobin, and insulin, and related to hepatitis B virus.

The clones of the present invention identify specific loci within the genome. By choosing clones that identify sites having multiple alleles which occur frequently in the population, a system is developed easily whereby an individual, or part thereof, can be identified with virtual certainty. For example, using five different ten allele loci in a panmictic population in which each allele has a frequency of about 0.1, the frequency of individuals with a specific pattern is expected to be no greater than 1 in 300 million. As a result, misidentification is unlikely.

The accurate method of genetic determination has usefulness in several different contexts. As mentioned above, specific genetic identification is useful to determine paternity. Other areas in which the system of the present invention will find application include determining monozygosity versus heterozygosity in twins, monitoring bone marrow transplants, forensics, identification of disease genes and gene mapping. In each of those contexts, identification with virtual certainty is provided.

It will be appreciated that the methods and compositions of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within the scope of the invention.

What is claimed is:

1. A nucleic acid fragment selected from the group consisting of pYNH24, the VNTR-containing fragment of pYNH24, a nucleic acid fragment having substantial sequence homology to said VNTR-containing fragment and a nucleic acid fragment which is capable of hybridizing to the single locus specified by pYNH24.

2. A nucleic acid fragment selected from the group consisting of pCMM6, the VNTR-containing fragment of pCMM6, a nucleic acid fragment having substantial sequence homology to said VNTR-containing fragment and a nucleic acid fragment which is capable of hybridizing to the single locus specified by pCMM6.

3. A nucleic acid fragment selected from the group consisting of pCMM66, the VNTR-containing fragment of pCMM66, a nucleic acid fragment having substantial sequence homology to said VNTR-containing fragment and a nucleic acid fragment which is capable of hybridizing to the single locus specified by pCMM66.

4. A nucleic acid fragment selected from the group consisting of cCMM77, the VNTR-containing fragment of cCMM77, a nucleic acid fragment having substantial sequence homology to said VNTR-containing fragment and a nucleic acid fragment which is capable of hybridizing to the single locus specified by cCMM77.

5. A nucleic acid fragment selected from the group consisting of pCMM86, the VNTR-containing fragment of pCMM86, a nucleic acid fragment having substantial sequence homology to said VNTR-containing fragment and a nucleic acid fragment which is capable of hybridizing to the single locus specified by pCMM86.

6. A nucleic acid fragment selected from the group consisting of pMLJ14, the VNTR-containing fragment of pMLJ14, a nucleic acid fragment having substantial sequence homology to said VNTR-containing fragment and a nucleic acid fragment which is capable of hybridizing to the single locus specified by pMLJ14.

7. A nucleic acid fragment selected from the group consisting of cMLJ205, the VNTR-containing fragment of cMLJ205, a nucleic acid fragment having substantial sequence homology to said VNTR-containing fragment and a nucleic acid fragment which is capable of hybridizing to the single locus specified by cMLJ205.

8. A nucleic acid fragment selected from the group consisting of pYNZ22, the VNTR-containing fragment of pYNZ22, a nucleic acid fragment having substantial sequence homology to said VNTR-containing fragment and a nucleic acid fragment which is capable of hybridizing to the single locus specified by pYNZ22.

9. A nucleic acid fragment selected from the group consisting of pJCZ3.1, the VNTR-containing fragment of pJCZ3.1, a nucleic acid fragment having substantial sequence homology to said VNTR-containing fragment and a nucleic acid fragment which is capable of hybridizing to the single locus specified by pJCZ3.1.

10. A nucleic acid fragment selected from the group consisting of pJCZ16.2, the VNTR-containing fragment of pJCZ16.2, a nucleic acid fragment having substantial sequence homology to said VNTR-containing fragment and a nucleic acid fragment which is capable of hybridizing to the single locus specified by pJCZ16.2.

11. A nucleic acid fragment selected from the group consisting of pJCZ67, the VNTR-containing fragment of pJCZ67, a nucleic acid fragment having substantial sequence homology to said VNTR-containing fragment and a nucleic acid fragment which is capable of hybridizing to the single locus specified by pJCZ67.

12. A nucleic acid fragment selected from the group consisting of pYNZ21, the VNTR-containing fragment of pYNZ21, a nucleic acid fragment having substantial sequence homology to said VNTR-containing fragment and a nucleic acid fragment which is capable of hybridizing to the single locus specified by pYNZ21.

13. A nucleic acid fragment selected from the group consisting of pCMM101, the VNTR-containing fragment of pCMM101, a nucleic acid fragment having substantial sequence homology to said VNTR-containing fragment and a nucleic acid fragment which is capable of hybridizing to the single locus specified by pCMM101.

14. A nucleic acid fragment selected from the group consisting of cEFD64, the VNTR-containing fragment of cEFD64, a nucleic acid fragment having substantial sequence homology to said VNTR-containing fragment and a nucleic acid fragment which is capable of hybridizing to the single locus specified by cEFD64.

15. A nucleic acid fragment selected from the group consisting of cEFD52, the VNTR-containing fragment of cEFD52, a nucleic acid fragment having substantial sequence homology to said VNTR-containing fragment and a nucleic acid fragment which is capable of hybridizing to the single locus specified by cEFD52.

16. A nucleic acid fragment selected from the group consisting of pEFD139, the VNTR-containing fragment of pEFD139, a nucleic acid fragment having substantial sequence homology to said VNTR-containing fragment and a nucleic acid fragment which is capable of hybridizing to the single locus specified by pEFD139.

17. A nucleic acid fragment selected from the group consisting of pEFD126.3, the VNTR-containing fragment of pEFD126.3, a nucleic acid fragment having substantial sequence homology to said VNTR-containing fragment and a nucleic acid fragment which is capable of hybridizing to the single locus specified by pEFD126.3.

18. A nucleic acid fragment selected from the group consisting of pTHH33, the VNTR-containing fragment of pTHH33, a nucleic acid fragment having substantial sequence homology to said VNTR-containing fragment and a nucleic acid fragment which is capable of hybridizing to the single locus specified by pTHH33.

19. A nucleic acid fragment selected from the group consisting of pTHH59, the VNTR-containing fragment of pTHH59, a nucleic acid fragment having substantial sequence homology to said VNTR-containing fragment and a nucleic acid fragment which is capable of hybridizing to the single locus specified by pTHH59.

20. A nucleic acid fragment selected from the group consisting of cMHZ47, the VNTR-containing fragment of cMHZ47, a nucleic acid fragment having substantial sequence homology to said VNTR-containing fragment and a nucleic acid fragment which is capable of hybridizing to the single locus specified by cMHZ47.

21. A nucleic acid fragment selected from the group consisting of pMHZ10, the VNTR-containing fragment of pMHZ10, a nucleic acid fragment having substantial sequence homology to said VNTR-containing fragment and a nucleic acid fragment which is capable of hybridizing to the single locus specified by pMHZ10.

22. A nucleic acid fragment selected from the group consisting of pMHZ13, the VNTR-containing fragment of pMHZ13, a nucleic acid fragment having substantial sequence homology to said VNTR-containing fragment and a nucleic acid fragment which is capable of hybridizing to the single locus specified by pMHZ13.

23. A nucleic acid fragment selected from the group consisting of cYNA13, the VNTR-containing fragment of cYNA13, a nucleic acid fragment having substantial sequence homology to said VNTR-containing fragment and a nucleic acid fragment which is capable of hybridizing to the single locus specified by cYNA13.

24. A nucleic acid fragment selected from the group consisting of cYNA4, the VNTR-containing fragment of cYNA4, a nucleic acid fragment having substantial sequence homology to said VNTR-containing fragment and a nucleic acid fragment which is capable of hybridizing to the single locus specified by cYNA4.

25. A nucleic acid fragment selected from the group consisting of cKKA39, the VNTR-containing fragment of cKKA39, a nucleic acid fragment having substantial sequence homology to said VNTR-containing fragment and a nucleic acid fragment which is capable of hybridizing to the single locus specified by cKKA39.

26. A nucleic acid fragment selected from the group consisting of pMCT118, the VNTR-containing fragment of pMCT118, a nucleic acid having substantial sequence homology to said VNTR-containing fragment and a nucleic acid fragment which is capable of hybridizing to the single locus specified by pMCT118.

27. A nucleic acid fragment selected from the group consisting of pCMI327, the VNTR-containing fragment of pCMI327, a nucleic acid fragment having substantial sequence homology to said VNTR-containing fragment and a nucleic acid fragment which is capable of hybridizing to the single locus specified by pCMI327.

28. A nucleic acid fragment selected from the group consisting of pMCOB17, the VNTR-containing fragment of pMCOB17, a nucleic acid fragment having substantial sequence homology to said VNTR-containing fragment and a nucleic acid fragment which is capable of hybridizing to the single locus specified by pMCOB17.

29. A nucleic acid fragment selected from the group consisting of pRMU3, the VNTR-containing fragment of pRMU3, a nucleic acid fragment having substantial sequence homology to said VNTR-containing fragment and a nucleic acid fragment which is capable of hybridizing to the single locus specified by pRMU3.

30. A nucleic acid fragment selected from the group consisting of pEKMDA2I, the VNTR-containing fragment of pEKMDA2I, a nucleic acid fragment having substantial sequence homology to said VNTR-containing fragment and a nucleic acid fragment which is capable of hybridizing to the single locus specified by pEKMDA2I.

31. A nucleic acid fragment selected from the group consisting of cTBQ7, the VNTR-containing fragment of cTBQ7, a nucleic acid fragment having substantial sequence homology to said VNTR-containing fragment and a nucleic acid fragment which is capable of hybridizing to the single locus specified by cTBQ7.

32. A clone set which comprises the clones pYNH24, pCMM6, pCMM66, cCMM77, pCMM86, pMLJ14, cMLJ205, pYNZ22, pJCZ3.1, pJCZ16.2, pJCZ67, pYNZ21, pCMM101, cEFD64, cEFD52, pEFD139, pEFD126.3, pTHH33, pTHH59, cMHZ47, pMHZ10, pMHZ13, cYNA13, cYNA4, cKKA39, pMCT118, pCMI327, pEKMDA2I, pRMU3, pMCOB17, CTBQ7, nucleic acid fragments capable of hybridizing to the insert and nucleic acid fragments capable of hybridizing to the insert to the single locus specified thereby.

33. The clone set of claim 32 wherein said clones are pYNH24, pCMM6, pCMM66, cCMM77, pCMM86, pMLJ14, cMLJ205, pYNZ22, pJCZ3.1, pJCZ16.2, pJCZ67, pYNZ21, pCMM101, cEFD64, cEFD52, pEFD139, pEFD126.3, pTHH33, pTHH59, cMHZ47, pMHZ10, pMHZ13, cYNA13, cYNA4, cKKA39, pMCT118, pCMI327, pEKMDA2I, pRMU3, pMCOB17 and CTBQ7.

34. A clone set which comprises at least two of the clones selected from the group consisting of pYNH24, pCMM6, pCMM66, cCMM77, pCMM86, pMLJ14, cMLJ205, pYNZ22, pJCZ3.1, pJCZ16.2, pJCZ67, pYNZ21, pCMM101, cEFD64, cEFD52, pEFD139, pEFD126.3, pTHH33, pTHH59, cMHZ47, pMHZ10, pMHZ13, cYNA13, cYNA4, cKKA39, pMCT118, pCMI327, pEKMDA2I, pRMU3, pMCOB17, CTBQ7, nucleic acid fragments capable of hybridizing to the insert and nucleic acid fragments capable of hybridizing to the insert to the single locus specified thereby.

35. The clone set of claim 34 wherein said clones are more than 50 map units or cM apart.

36. The clone set of claim 34 wherein no more than one clone maps to any one chromosomal arm.

37. The clone set of claim 34 wherein no more than one clone maps to any one chromosome.

38. The clone set of claim 34 comprising pYNH24, pCMM101, pMLJ14, cTBQ7, pCMM66, pCMM73 and pCMM86.

* * * * *

UNITED STATES PATENT AND TRADEMARK OFFICE
CERTIFICATE OF CORRECTION

PATENT NO. : 4,963,663
DATED : October 16, 1990
INVENTOR(S) : Raymond L. WHITE et al.

It is certified that error appears in the above-identified patent and that said Letters Patent is hereby corrected as shown below:

In claim 32, at column 35, line 7, please change "to the insert to the single locus specified thereby" to read -- to the single locus specified by the insert --.

In claim 34, at column 36, line 8, please change "to the insert to the single locus specified thereby" to read -- to the single locus specified by the insert --.

In claim 38, at column 36, line 16, please change "73" to read -- 77 --.

Signed and Sealed this

Eighth Day of December, 1992

*Attest:*

DOUGLAS B. COMER

*Attesting Officer*     *Acting Commissioner of Patents and Trademarks*